United States Patent [19]

Trinh

[11] Patent Number: 5,246,611

[45] Date of Patent: * Sep. 21, 1993

[54] NON-DESTRUCTIVE CARRIERS FOR CYCLODEXTRIN COMPLEXES

[75] Inventor: Toan Trinh, Maineville, Ohio

[73] Assignee: The Procter & Gamble Company, Cincinnati, Ohio

[*] Notice: The portion of the term of this patent subsequent to Aug. 18, 2009 has been disclaimed.

[21] Appl. No.: 770,757

[22] Filed: Oct. 4, 1991

Related U.S. Application Data

[63] Continuation of Ser. No. 521,304, May 9, 1990, abandoned.

[51] Int. Cl.$^5$ .............................................. D06M 10/08
[52] U.S. Cl. .................................... 252/8.6; 252/8.75; 252/8.9
[58] Field of Search ..................... 252/8.6, 8.75, 8.9

[56] References Cited

U.S. PATENT DOCUMENTS

| | | | |
|---|---|---|---|
| 3,442,692 | 5/1965 | Gaiser .................................. | 252/8.6 |
| 3,846,551 | 11/1974 | Mifune et al. ...................... | 424/180 |
| 4,024,223 | 5/1977 | Noda et al. ......................... | 424/180 |
| 4,228,160 | 10/1980 | Szejtli et al. ....................... | 424/180 |
| 4,298,138 | 10/1981 | Boden ................................. | 426/534 |
| 4,348,416 | 9/1982 | Boden ................................. | 426/3 |
| 4,365,061 | 12/1982 | Szejtli et al. ....................... | 536/103 |
| 4,371,673 | 2/1983 | Pitha .................................. | 525/426 |
| 4,380,626 | 4/1983 | Szejtli et al. ....................... | 536/103 |
| 4,438,106 | 3/1984 | Wagu et al. ........................ | 424/180 |
| 4,474,822 | 10/1984 | Sato et al. .......................... | 426/597 |
| 4,529,608 | 7/1985 | Szejtli et al. ....................... | 426/96 |
| 4,596,795 | 6/1986 | Pitha .................................. | 514/58 |
| 4,616,008 | 10/1986 | Hirai et al. ......................... | 514/200 |
| 4,663,316 | 5/1987 | Ninger et al. ...................... | 514/99 |
| 4,675,395 | 6/1987 | Fukazawa et al. ................. | 536/103 |
| 4,678,598 | 7/1987 | Ogino et al. ....................... | 252/174.17 |
| 4,727,064 | 2/1988 | Pitha .................................. | 514/58 |
| 4,727,824 | 3/1988 | Ducharme et al. ................ | 119/1 |
| 4,728,510 | 3/1988 | Shibanai et al. ................... | 424/94.5 |
| 4,732,759 | 3/1988 | Shibanai et al. ................... | 424/94.61 |
| 4,751,095 | 6/1988 | Karl et al. .......................... | 426/548 |
| 4,917,920 | 4/1990 | Ono et al. .......................... | 427/389.9 |
| 5,139,687 | 8/1992 | Borgher, Sr. et al. .............. | 252/8.6 |

FOREIGN PATENT DOCUMENTS

| | | |
|---|---|---|
| 251459 | 1/1988 | European Pat. Off. . |
| 3020269 | 1/1981 | Fed. Rep. of Germany . |
| 124452 | 7/1983 | Japan . |
| 128973 | 6/1986 | Japan . |
| 64-74297 | 3/1989 | Japan . |

OTHER PUBLICATIONS

CA102:137676 (Abstract Only); Chemical Abstracts Citation, Szente Suppositories Containing Beta-Cyclodextrin Complexes.

(Author Unknown), Product Data, American Maize--Products Company, "Preparation of Cyclodextrin Complexes" (no date indicated).

Hashimoto, H. "Studies on the Industrial Production and Application of Cyclodextrins", Denpun Kagaku (Starch Science), vol. 36, No. 1, (1989) pp. 35-42.

Hashimoto, H. "Application of Cyclodextrins to Foods, Toiletries, and Other Products in Japan II," Eusuiko Sugar Refining Co., Ltd. Publication (1988).

Primary Examiner—Olik Chaudhuri
Assistant Examiner—C. Everhart
Attorney, Agent, or Firm—Robert B. Aylor

[57] ABSTRACT

Cyclodextrin complex is suspended in polyalkylene glycol carrier material that does not displace the included material. The preferred perfume/cyclodextrin complexes, either alone or admixed with solvent (e.g., water), are preferably suspended in the carrier and then incorporated into solid, dryer-activated, fabric treatment (conditioning) compositions, preferably containing fabric softeners, more preferably cationic and/or nonionic fabric softeners. The perfume complexes provide fabrics with perfume benefits when they are rewetted after drying. Volatile perfume materials, including those materials that are commonly associated with "freshness" can be applied to the fabrics in an effective way.

30 Claims, No Drawings

NON-DESTRUCTIVE CARRIERS FOR CYCLODEXTRIN COMPLEXES

This is a continuation of application Ser. No. 07/521,304, filed on May 9, 1990, now abandoned.

TECHNICAL FIELD

The present invention relates to an improvement in processes using cyclodextrin complexes, especially perfume/cyclodextrin complexes, and/or compositions containing said complexes.

BACKGROUND OF THE INVENTION

The present invention relates to an improvement in consumer products (compositions), especially solid consumer products (compositions), and processes for making said products, containing solid cyclodextrin inclusion complexes of actives, which are typically hydrophobic materials like perfumes, flavoring materials, pharmaceutical actives, antibacterials, bleaches, etc., said products, and/or compositions, being, preferably, either in particulate form; compounded with other materials in solid form, e.g., tablets, pellets, agglomerates, gel sticks, etc.; or attached to a substrate.

The use of cyclodextrin as a complexing agent for materials is well documented, including the disclosures in U.S. Pat. Nos.: 4,348,416, Boden (flavoring material for use in chewing gum, dentifrices, cosmetics, etc.); 4,296,138, Boden (similar to 4,348,416); 4,265,779, Gandolfo et al. (suds suppressors for use in detergent compositions); 3,816,393, Hayashi et al. (prostaglandins for use as pharmaceuticals); 3,846,551, Mifune et al. (insecticidal and acaricidal compositions); 4,024,223, Noda et al. (menthol, methyl salicylate, etc.); 4,054,736, Hayashi et al. (similar to 3,816,393); 4,073,931, Akito et al. (nitroglycerin/cyclodextrin complexes); 4,228,160, Szjetli et al. (indomethacin); 4,247,535, Bernstein et al. (cyclodextrin complexes of complement inhibitors); 4,268,501, Kawamura et al. (cyclodextrin complexes of anti-asthmatic actives); 4,365,061, Szejtli et al. (strong inorganic oxyacids complexes); 4,371,673, Pitha (retinoids); 4,380,626, Szejtli et al. (hormonal plant growth regulator); 4,438,106, Wagu et al. (long chain fatty acids useful to reduce cholesterol); 4,474,822, Sato et al. (cyclodextrin/tea essence complexes); 4,529,608, Szejtli et al. (honey aroma); 4,547,365, Kubo et al. (cyclodextrin/hair-waving-active complexes); 4,548,811, Kubo et al. (waving lotion); 4,596,795, Pitha (sex hormones); 4,616,008, Hirai et al. (antibacterial complexes); 4,636,343, Shibanai (insecticide complexes); 4,663,316, Ninger et al. (antibiotics); 4,675,395, Fukazawa et al. (hinokitiol); 4,732,759 and 4,728,510, Shibanai et al. (complexes of bath additives); and 4,751,095, Karl et al. (aspartame/cyclodextrin complex), all of said patents being incorporated by reference. There is however, need for improvements in the preparation of products containing said complexes and for improved water-soluble forms containing said complexes. There is a special need for intermediate compositions that can facilitate handling the complexes.

SUMMARY OF THE INVENTION

It has now been discovered that certain materials like polyalkylene glycols, e.g., polyethylene and/or polypropylene glycols, can be used as carriers, and especially liquid carriers, for cyclodextrin complexes, e.g., complexes of cyclodextrins with perfumes, while minimizing the destruction of such complexes. Compositions comprising both carrier and complex can be used, e.g., in the preparation of dryer-activated fabric treatment (conditioning) compositions, e.g., softening, compositions, including those softening compositions that are detergent compatible, as described hereinafter. Cyclodextrin complexes have been disclosed generically as set forth hereinbefore and have been suggested for use in a variety of products. However, it is desirable to have the said complexes suspended in a liquid carrier (including molten solids) that facilitates either their incorporation into other compositions, e.g., solid, dryer-activated, fabric conditioning compositions, or the formation of solid carrier/complex compositions as set forth hereinafter. Preparation of such compositions involves distributing the complexes in an even manner and attaining even distribution can be difficult when the complex is in a particulate form. Also, it is desirable to have pumpable mixtures to permit easy handling and processing and avoid the need for extra equipment to handle powders.

Cyclodextrin molecules have an apolar, hydrophobic cavity which can contain hydrophobic molecules called guest molecules (or the hydrophobic portions of molecules) of appropriate sizes to fit inside the cavity and thus form inclusion complexes. One would therefore be led to believe that polar solvents would not have a sufficient affinity for the cavity and would not displace the more hydrophobic guests. In the search for a compatible, nondestructive, liquid or meltable carrier for the cyclodextrin complexes it has been found that most polar solvents, e.g., the hydroxy and polyhydroxy solvents, e.g., low molecular weight alcohols, ethylene glycol, 1,2-propanediol, glycerol and molten sorbitol, at least partially decompose the inclusion complexes and release some of the guest molecules. Surprisingly, it is now found that some liquid or meltable solids, as described hereinafter, can be used to make pumpable, fluid slurries of cyclodextrin complexes at typical process temperatures, e.g., at about 100° C. or lower, without decomposing the cyclodextrin complexes.

Cyclodextrin complexes can be dispersed in polyalkylene glycol carriers that are preferably either liquid or molten at temperatures from about room temperature up to about 100° C. Solvents such as water used in the formation of the said complexes can also be present. The resulting compositions are pumpable fluids which are easier to handle during subsequent processing. For example, a preferred composition and process comprises spraying the molten mixtures of (a) active/cyclodextrin complex, and (b) normally solid polyalkylene, e.g., polyethylene, glycol material onto a solid substrate surface, then letting the droplets solidify on said surface. Another preferred composition and process comprises forming the complex in the presence of a limited amount of, e.g., water, then, without the solvent being removed, the normally solid, polyalkylene, preferably polyethylene, glycol material is admixed in molten form with the complex and water mixture to form a pumpable mixture that can be used directly to form solid compositions that would ordinarily not be compatible with the complex and water mixture alone.

Thus, in its broadest aspects, the invention relates to the method of incorporating an effective amount of cyclodextrin complex into a polyalkylene glycol carrier that is, or can be made, liquid and that does not significantly decompose the complex (i.e., is compatible with the complex).

DESCRIPTION OF THE INVENTION

1. CYCLODEXTRINS

As used herein, the term "cyclodextrin" (CD) includes any of the known cyclodextrins such as unsubstituted cyclodextrins containing from six to twelve glucose units, especially, alpha-, beta-, gamma-cyclodextrins, and mixtures thereof, and/or their derivatives, and/or mixtures thereof, that are capable of forming inclusion complexes with perfume ingredients. Alpha-, beta-, and gamma-cyclodextrins can be obtained from, among others, American Maize-Products Company (Amaizo), Corn Processing Division, Hammond, Ind.; and Roquette Corporation, Gurnee, Ill. There are many derivatives of cyclodextrins that are known. Representative derivatives are those disclosed in U.S. Pat. Nos: 3,426,011, Parmerter et al., issued Feb. 4, 1969; 3,453,257, 3,453,258, 3,453,259, and 3,453,260, all in the names of Parmerter et al., and all issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,638,058, Brandt et al., issued Jan. 20, 1987; 4,746,734, Tsuchiyama et al., issued May 24, 1988; and 4,678,598, Ogino et al., issued Jul. 7, 1987, all of said patents being incorporated herein by reference. Examples of cyclodextrin derivatives suitable for use herein are methyl-$\beta$-CD, hydroxyethyl-$\beta$-CD, and hydroxypropyl-$\beta$-CD of different degrees of substitution (D.S.), available from Amaizo and from Aldrich Chemical Company, Milwaukee, Wis. Water-soluble derivatives are also highly desirable.

The individual cyclodextrins can also be linked together, e.g., using multifunctional agents to form oligomers, cooligomers, polymers, copolymers, etc. Examples of such materials are available commercially from Amaizo and from Aldrich Chemical Company ($\beta$-CD/epichlorohydrin copolymers).

It is also desirable to use mixtures of cyclodextrins and/or precursor compounds to provide a mixture of complexes. Such mixtures, e.g., can provide more even odor profiles by encapsulating a wider range of perfume ingredients and/or preventing formation of large crystals of said complexes. Mixtures of cyclodextrins can conveniently be obtained by using intermediate products from known processes for the preparation of cyclodextrins including those processes described in U.S. Pat. Nos.: 3,425,910, Armbruster et al., issued Feb. 4, 1969; 3,812,011, Okada et al., issued May 21, 1974; 4,317,881, Yagi et al., issued Mar. 2, 1982; 4,418,144, Okada et al., issued Nov. 29, 1983; and 4,738,923, Ammeraal, issued Apr. 19, 1988, all of said patents being incorporated herein by reference. Preferably at least a major portion of the cyclodextrins are alpha-cyclodextrin, beta-cyclodextrin, and/or gamma-cyclodextrin, more preferably beta-cyclodextrin. Some cyclodextrin mixtures are commercially available from, e.g., Ensuiko Sugar Refining Company, Yokohama, Japan.

2. THE ACTIVES

Many different active materials can be complexed with cyclodextrins as set out in the patents incorporated hereinbefore and hereinafter by reference. Perfumes are a highly desirable active material that can usually benefit from protection and that can be complexed, especially when the perfume is relatively hydrophobic. Flavoring active materials are like perfumes in that they tend to be adversely affected by the environment and require protection. Another type of active material that is often complexed with cyclodextrins is a pharmaceutical active that needs to be protected from the environment. Yet other types of active material that are advantageously complexed are oxidation or reduction active that interacts with other materials that are present and biocontrol actives. In general, active materials that form complexes with cyclodextrin and are released by the action of water are useful in the practice of this invention.

A. Perfumes

Detergents; fabric softening products; cosmetics, including antiperspirants, hair and skin care products; and disposable absorbent products like diapers and catamenial articles, all typically contain some perfume to provide some fragrance to provide an olfactory aesthetic benefit and/or to serve as a signal that the product is effective.

The perfume in such products is often lost before it is needed. Perfumes can be subject to damage and/or loss by the action of, e.g., oxygen, light, heat, etc. For example, due to the high energy input and large air flow in the drying process used in the typical automatic laundry dryers, a large part of the perfume provided by dryer-added softener products has been lost out the dryer vent. Even for less volatile components, as described hereinafter, only a small fraction remains on the fabrics after the drying cycle. The loss of the highly volatile fraction of the perfume, as described hereinafter, is much higher. Usually the loss of the highly volatile fraction is practically total. Due to this effect, many perfumes used in, e.g., dryer-added fabric softener compositions, have been composed mainly of less volatile, high boiling (having high boiling points), perfume components to maximize survival of the odor character during storage and use and thus provide better "substrate substantivity." The main function of a small fraction of the highly volatile, low boiling (having low boiling points), perfume components in these perfumes is to improve the fragrance odor of the product itself, rather than impacting on the subsequent substrate, e.g., fabric or body, odor. However, some of the volatile, low boiling perfume ingredients can provide a fresh and clean impression to the substrate, and it is highly desirable that these ingredients be deposited and present on the substrate.

Perfumes used in cosmetics and disposable absorbent products also tend to be lost prematurely. It is highly desirable to have volatile perfume ingredients available until they are released by water contained in, e.g., urine, sweat, menses, etc.

The perfume ingredients and compositions of this invention are the conventional ones known in the art. Selection of any perfume component, or amount of perfume, is based solely on aesthetic considerations. Suitable perfume compounds and compositions can be found in the art including U.S. Pat. Nos.: 4,145,184, Brain and Cummins, issued Mar. 20, 1979; 4,209,417, Whyte, issued Jun. 24, 1980; 4,515,705, Moeddel, issued May 7, 1985; and 4,152,272, Young, issued May 1, 1979, all of said patents being incorporated herein by reference. Many of the art recognized perfume compositions are relatively substantive, as described hereinafter, to maximize their odor effect on substrates. However, it is a special advantage of perfume delivery via the perfume/cyclodextrin complexes that nonsubstantive perfumes are also effective.

A substantive perfume is one that contains a sufficient percentage of substantive perfume materials so that when the perfume is used at normal levels in products, it deposits a desired odor on the treated substrate. In general, the degree of substantivity of a perfume is roughly proportional to the percentage of substantive perfume material used. Relatively substantive perfumes contain at least about 1%, preferably at least about 10%, substantive perfume materials.

Substantive perfume materials are those odorous compounds that deposit on substrates via the treatment process and are detectable by people with normal olfactory acuity. Such materials typically have vapor pressures lower than that of the average perfume material. Also, they typically have molecular weights of about 200 or above, and are detectable at levels below those of the average perfume material.

Perfumes can also be classified according to their volatility, as mentioned hereinbefore. The highly volatile, low boiling, perfume ingredients typically have boiling points of about 250° C. or lower. Many of the more moderately volatile perfume ingredients are also quickly lost. For example, substantially all of such perfumes are lost in the drying cycle of a typical laundry process. The moderately volatile perfume ingredients are those having boiling points of from about 250° C. to about 300° C. The less volatile, high boiling, perfume ingredients referred to hereinbefore are those having boiling points of about 300° C. or higher. A significant portion of even these high boiling perfume ingredients, considered to be highly substantive, can be lost, e.g., during a laundry drying cycle, and it is desirable to have means to retain more of these ingredients on the substrates. Many of the perfume and flavor ingredients as discussed hereinafter, along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiarybutyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclopenta-gama-2benzopyran), hexyl cinnamic aldehyde, lyral (4(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

Cyclodextrin inclusion complexes (perfume/cyclodextrin, or perfume/CD, complexes), as described hereinafter, of the high boiling, the moderately volatile, and the low boiling perfume ingredients are stable (a) throughout the mixing of the complexes with the remainder of the compositions, e.g., the molten fabric softener mixes, especially when the fabric softener mixes contain some clay, and the coating of the resulting fabric softening compositions onto flexible substrates to form fabric conditioning sheets, (b) during the application of the composition to the substrate, e.g., during the drying of the wet fabrics in tumble dryers, and (c) during use, e.g., when the cosmetic is on the skin or during the wear of the dry fabrics. The content of the perfume in the complex is typically from about 5% to about 15%, more normally from about 7% to about 10%.

B. Flavors

Flavoring materials are desirable actives to use in the form of cyclodextrin complexes. As used herein, the term "flavors" also includes spices, flavor enhancers, etc., that contribute to the overall flavor perception. Advantages of cyclodextrin/flavor complexes include: (1) the protection of active ingredients from reactions induced by heat, light, and/or oxygen; (2) less loss of flavor by volatilization and/or sublimation; and (3) providing stable, standardized, powders that contain flavors to reduce packaging and/or labor costs. In the household, the flavoring materials can be stored longer and the measurement is more precise, since the flavor content remains more stable. At the same time, the natural material content of some flavors can be reduced to minimize the potential for allergic reactions and the risk of microbial contamination can be reduced. Minimization of preparation time is another benefit that is especially important. All of these benefits are also important to commercial food preparation. The reduction in food handling saves labor and minimizes the potential for contamination of the food.

The cyclodextrin/flavor complexes are readily prepared as discussed hereinafter, and the cyclodextrin complexes do not adversely affect the appearance, texture, and/or flavor of the food. The texture may, in some instances, be beneficially thickened, e.g., as in drinks and soups prepared from mixes. The flavor/cyclodextrin complexes lose very little of their flavor active content in storage. If stability in the presence of extreme heat is desired, the complexes can be coated with, e.g., hardened fat, polymers, etc.

The content of the flavor in the complex is typically from about 5% to about 15%, more often from about 7% to about 10%. Flavor actives, like perfume actives, normally consist of several components. While it is usually important to incorporate the active into the complex without changing the composition, it is also possible to complex only the more vulnerable components and thereby minimize the level of complex required.

Specific examples of flavors and flavor enhancers include those disclosed in U.S. Pat. No. 4,348,416, Boden, incorporated herein by reference. I.e., organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid and 2-methyl-3-pentenoic acid; ketones and aldehydes, e.g., 2-methyl-3-ketofuran, acetophenone, acetone, acetyl methyl carbinol, acrolein, n-butanal, crotonal, diacetyl, 2-methylbutanal, beta-beta-dimethyl acrolein, methyl n-amyl ketone, n-hexanal, 2-hexanal, isopentenal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl- 2-hexenal, 2-phenyl-2-pentenal, furfural, 5-methyl-furfural, cinnamaldehyde, beta-cyclohomocitral, 2-pentanone, 2-pentenal and propanal, alcohols such as 1-butanol, benzyl alcohol, iso-borneol, trans-2-buten-1-ol, ethanol, geraniol, 1-hexanol, 2-heptanol, trans-2-hexen-1-ol, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, menthol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, iso-amyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alphaphellandrene, beta-phellandrene, p-cymene, alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils and extracts such as jasmine absolute, cassia oil, cinnamon bark oil, black pepper oleoresin, tumeric oil, oil of black pepper, rose absolute, orris absolute, oil of cubeb, oil of coriander, oil of pimento leaf, oil of patchouli, oil of nutmeg, ginger oil, lemon essential oil, dill oil, lemon grass oil, oil of valerion, marjoram oil, raspberry oil, cinnamon oil, carrot oil, anise oil, orange oil, thyme oil, peppermint oil, sweet cumin oil, celery oil, garlic oil, onion oil, tarragon oil, caraway oil, basil oil, bay leaf oil, mustard oil, sage, tea extract, coffee extract, safran oil, Bulgarian rose, capsicum, yara yara, vanilla, nut oils and the synthetic versions of these natural oils and extracts; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperdine.

Specific examples of the invention include the use of the complexes in the preparation of powdered mixes, e.g., drink mixes. For example, tea extract, synthetic sweeteners, and/or one or more flavors such as bergamot, jasmine, lemon oil, peppermint oil, etc., can be added to a powdered instant tea mix and the resulting product has a more stable flavor profile and the flavor is released immediately to allow for full enjoyment of the flavor. Examples of tea mixtures and instant tea mixes can be found in U.S. Pat. No. 4,474,822, Sato et al., issued Oct. 2, 1984; and in Brit. Pat. 2,074,838, to Chinoin Gyogyszer, issued Nov. 11, 1981, said patents being incorporated herein by reference.

Similar advantages are found when a flavor ingredient such as a beef extract is complexed and added to a powdered soup mix. The advantage of the complex is especially apparent for those flavors that are prone to decomposition and/or require considerable time to prepare.

Dairy products are especially desirable to complex. Butter flavor is especially prone to destruction during storage. The use of complexes is especially desirable when refrigeration is not possible or is not dependable.

The use of complexes in "prepared foods" that are prepared and packaged and then sold after a period of time has elapsed, is especially advantageous. Uncomplexed flavor components are often changed after storage resulting in a "less fresh" flavor.

Complexed flavors are also very useful in other products like chewing gum, toothpastes and powders, medicines, etc., where the product is used in the mouth, but not for food.

C. Pharmaceuticals

Another class of actives that is highly desirable to complex is pharmaceutical materials (drugs). Drugs that have been suggested for complexation include those described in the patents incorporated by reference hereinbefore, and especially U.S. Pat. No. 4,727,064, Pitha, issued Feb. 23, 1988, incorporated herein by reference. The list includes ibuprofen, acetylsalicylic acid (or its salts), acetamidophen, apomorphine, butylated hydroxytoluene, chlorthalidone, cholecalciferol, dexamethasone, dicumarol, digoxin, diphenylhydantoin, estradiol, estriol, ethinylestradiol-3-methyl ether, ethisterone, furosemide, hydroflumethiazide, indomethacin, iproniazid phosphate, 17-methyltestosterone, nitroglycerin, norethindrone, oubain, oxprenolol, progesterone, retinal, trans-retinoic acid and/or its salts, retinol, spironolactone, sulpiride, testosterone, theophylline, aryclovir, cloridine HCl, etc.

The complexation of drugs is highly desirable since loss of activity can mean the drug will be ineffective if the prescribed dose is not administered.

D. Biocontrol Agents

Another class of actives that is highly desirable to complex is biocontrol agents. Biocontrol agents comprise biocides, antimicrobials, bactericides, fungicides, algaecides, mildewcides, disinfectants, antiseptics, insecticides, vermicides, plant growth hormones, etc. Such agents having suitable molecular structures can be complexed with cyclodextrins, and released either externally to the environment, such as on fabrics, skin (including on wounds), leaves, and/or the ground, as in the case of fungicides, disinfectants, antiseptics, plant growth hormones, etc., or internally into the body as in the case of bactericides and/or vermicides.

3. COMPLEX FORMATION

The complexes of this invention are formed in any of the ways known in the art. Typically, the complexes are formed either by bringing the perfume and the cyclodextrin together as solutions in suitable solvents, preferably water, or in suspension or by kneading the ingredients together in the presence of a suitable, preferably minimal, amount of solvent, preferably water. Other polar solvents such as ethylene glycol, propylene glycol, diethylene glycol, triethylene glycol, 2-methoxy ethanol, 2-ethoxy ethanol, glycerine, dimethylsulfoxide, dimethylformamide, 1,2-propanediol, ethanol, methanol, isopropanol, etc., and mixtures of said polar solvents with themselves and/or with water can be used as solvents for complex formation. The use of such solvents in complex formation has been disclosed in an article in *Chemistry Letters* by A. Harada and S. Takahashi, pp. 2089–2090 (1984), said article being incorporated herein by reference. The suspension/kneading method is particularly desirable because less solvent is needed and therefore less separation of the solvent is required. Suitable processes are disclosed in the patents incorporated hereinbefore by reference. Additional disclosures of complex formation can be found in Atwood, J. L., J. E. D. Davies & D. D. MacNichol, (Ed.): *Inclusion Compounds, Vol. III*, Academic Press (1984), especially Chapter 11; Atwood, J. L. and J. E. D. Davies (Ed.): *Proceedings of the Second International Symposium of Cyclodextrins* Tokyo, Japan, (July, 1984); *Cyclodextrin Technology*, J. Szejtli, Kluwer Academic Publishers (1988); all of said publications being incorporated by reference.

In general, active/cyclodextrin complexes have a molar ratio of active compound to cyclodextrin of 1:1. However, the molar ratio can be either higher or lower, depending on the molecular size of the active compound and the identity of the cyclodextrin compound. The molar ratio can be determined easily by forming a saturated solution of the cyclodextrin and adding the active to form the complex. In general the complex will precipitate readily. If not, the complex can usually be precipitated by the addition of electrolyte, change of pH, cooling, etc. The complex can then be analyzed to determine the ratio of active to cyclodextrin.

As stated hereinbefore, the actual complexes are determined by the size of the cavity in the cyclodextrin and the size of the active molecule. Although the normal complex is one molecule of active in one molecule of cyclodextrin, complexes can be formed between one molecule of active and two molecules of cyclodextrin when the active molecule is large and contains two portions that can fit in the cyclodextrin. Highly desirable complexes can be formed using mixtures of cyclodextrins since some actives like perfumes and flavor extracts are normally mixtures of materials that vary widely in size. It is usually desirable that at least a majority of the material be alpha-, beta-, and/or gamma-cyclodextrin, more preferably beta-cyclodextrin.

Processes for the production of cyclodextrins and complexes are described in U.S. Pat. Nos.: 3,812,011, Okada, Tsuyama, and Tsuyama, issued May 21, 1974; 4,317,881, Yagi, Kouno and Inui, issued Mar. 2, 1982; 4,418,144, Okada, Matsuzawa, Uezima, Nakakuki, and Horikoshi, issued Nov. 29, 1983; 4,378,923, Ammeraal, issued Apr. 19, 1988, all of said patents being incorporated herein by reference. Materials obtained by any of these variations are acceptable for the purposes of this invention. It is also acceptable to initially isolate the inclusion complexes directly from the reaction mixture by crystallization.

Continuous operation usually involves the use of supersaturated solutions, and/or suspension/kneading, and/or temperature manipulation, e.g., heating and then either cooling, freeze-drying, etc. The complexes can be dried or not depending on the next step in the process for making the desired composition. Incorporation of the complex/solvent (water) mixture in polyalkylene glycol carrier eliminates the need for a drying step. Thus, it is desirable to use the wet, undried complex slurry with a liquid carrier for improved handling and ease of incorporation into subsequent compositions. In general, the fewest possible process steps are used to avoid loss of active and excessive processing costs.

4. COMPLEX PARTICLE SIZES

The particle sizes of the complexes are selected according to the desired active, e.g., perfume release profile. Small particles, e.g., from about 0.01 μm to about 15 μm, preferably from about 0.01 μm to about 8 μm, more preferably from about 0.05 μm to about 5 μm, are desirable for providing a quick release of the perfume when the substrates, e.g., dried fabrics, are rewetted. It is a special benefit of this invention that small particles can be created and maintained by, e.g., dissolution of the cyclodextrin in the carrier. These small particles are also conveniently prepared initially by the suspension/kneading method. Larger particles, e.g., those having particle sizes of from about 15 μm to about 1,000 μm preferably from about 15 μm to about 250 μm, more preferably from about 15 μm to about 50 μm, are unique in that they can provide either slow release of active when the substrates are rewetted with a large amount of water or a series of active releases when the substrates are rewetted a plurality of times. They are also desirable for application directly to damp substrates. They release some active upon contact with damp substrates, but retain sufficient active to provide active effects when the substrates are rewetted. The larger particle size complexes are conveniently prepared by a crystallization method in which the complexes are allowed to grow, and large particles are ground to the desired sizes if necessary. Mixtures of small and large particles can give a broader active profile. Therefore, it can be desirable to have substantial amounts of particles both below and above 15 microns.

5. THE CARRIERS

Cyclodextrin complexes can be dispersed homogeneously in polyalkylene glycol carriers that are liquid or molten at less than about 100° C., especially polyalkylene glycol materials such as:

(A) Polyalkylene glycols and/or mixed polyalkylene glycols having average molecular weights (MW) of from about 400 to about 20,000, preferably between about 600 and about 10,000. Examples include:

polyethylene glycols, preferably having molecular weights of from about 1,000 to about 9,000, more preferably from about 1,400 to about 4,000;

polypropylene glycols, preferably having molecular weights of from about 600 to about 4,000;

poly(tetramethylene glycol), preferably having molecular weights of from about 1,000 to about 10,000;

mixed polyalkylene glycols such as poly(ethylene oxidepropylene oxide). Examples: average MW 1,100, E/P ratio 0.15:1; average MW 3,440, E/P ratio 0.33:1; average MW 2,920, E/P ratio 0.8:1; average MW 13,333, E/P ratio 3:1; and average MW 8,750, E/P ratio 5:1; and mixed polyalkylene glycol block copolymers such as HO—[CH$_2$CH$_2$O]$_x$—[CH$_2$CH(CH$_3$)O]$_y$—[CH$_2$CH$_2$O]$_x$—H and/or HO—[CH(CH$_3$)CH$_2$O]$_y$—[CH$_2$CH$_2$O]$_x$—[CH$_2$CH(CH$_3$)O]$_y$—H wherein the sum of the y's ranges from about 15 to about 70, and the ratio of the sum of the x's to the sum of the y's is from about 1:10 to about 11:10, preferably from about 1:2 to about 1:1. Examples include materials made by BASF Corporation and sold under the trade names of Pluronic ® and Pluronic R ® surfactants, respectively.

(B) C$_1$-C$_{22}$, preferably C$_1$-C$_4$ alkylated polyalkylene glycols [poly(alkylene glycol) mono- and dialkyl ethers], RO—(R$^2$O)$_n$—H and/or RO—(R$^2$O)$_n$—R, with each R being methyl, ethyl, propyl, or butyl; each R$^2$ being a C$_2$-C$_4$ alkylene group; and n ranging from 1 to about 200, with the percentage of polyalkylene glycol being preferably more than about 50%. Specific examples include:

RO—[CH$_2$CH(CH$_3$)O]$_m$—H, with R being methyl, ethyl, propyl, or butyl; and m being from 1 to about 200 (MW from about 90 to about 20,000);

RO—(CH$_2$CH$_2$O)$_n$—H, with each R being methyl, ethyl, propyl, or butyl, preferably methyl; and n being from about 2 to about 200 (MW from about 120 to about 9,000), preferably from about 15 to about 150 (MW from about 700 to about 6,700), more preferably from about 15 to about 100 (MW from about 700 to about 4,500); and/or RO—(CH$_2$CH$_2$O)$_n$—R, with each R being methyl, ethyl, propyl, or butyl; and n being from about 2 to about 200 (MW from about 134 to about 9,000), preferably from about 15 to about 150 (MW from about 700 to about 6,700), more preferably from about 15 to about 100 (MW from about 700 to about 4,500).

(C) Polyalkoxylated materials having an average molecular weight of from about 200 to about 20,000 and the weight percent of the polyalkoxy portion being from about 50% to about 99%. Specific examples include: Tetronic ® and Tetronic R ®; and Varstat 66 ®. Tetronic ® and Tetronic R ® are block copolymeric surfactants, manufactured by BASF Corporation. Tetronic ® surfactants have the general formula:

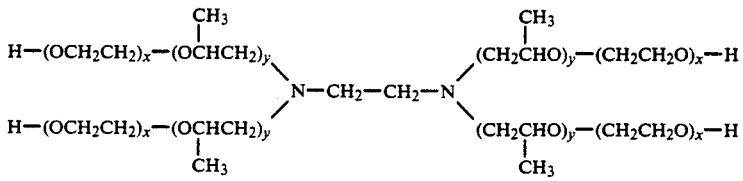

and Tetronic R ® surfactants have the general formula:

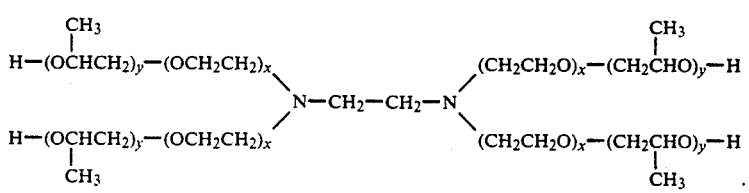

wherein the sum of the y's ranges from about 8 to about 120, and the ratio of the sum of the x's to the sum of the y's is from about 1:10 to about 11:10, preferably from about 1:2 to about 1:1.

Varstat 66 ®, sold by Sherex Chemical Company, has the formula

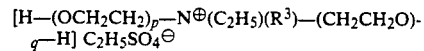

with R$^3$ being a C$_{12}$-C$_{18}$ alkyl or alkenyl radical, and with p+q being preferably from about 10 to about 30. Surfynol 465 ®, sold by Air Products and Chemicals, Inc., is an ethylene oxide adduct of 2,4,7,9,tetramethyl-5-decyn-4,7-diol of the formula

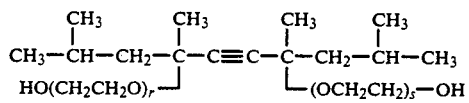

with r+s being about 8. In Surfynol 465 ® the weight percent of the polyethylene oxide portion is about 65%. The carriers can contain other moieties so long as they do not disrupt the complex excessively.

The weight ratio of the complex to the carrier is from about 1:1 to about 1:5, preferably from about 2:3 to about 1:3. The level of the carrier has to be relatively high so that the complex can be supported and the mixture of complex and carrier can be relatively fluid when the carrier is in a liquid state.

Preferred carriers are those that are solid at room temperature but can become molten or fluid below about 100° C., more preferably those that can become molten or fluid below about 80° C.

Specific examples are:

polyethylene glycols with an average MW of from about 600 to about 20,000;

poly(tetramethylene glycols) with an average MW of from about 1,000 to about 10,000; and poly(ethylene glycol) methyl ether with an average MW of from about 600 to about 20,000.

The complexes herein are desirably formed by a process, of the type described hereinbefore, in which cyclodextrin is mixed with the active, preferably perfume, in a limited amount of water, then the water is dried off by air or by lyophilization, as described hereinafter. The complex is then admixed with the liquid carrier material, or preferably with the molten normally solid carrier material, at a ratio of the complex to the carrier of from about 1:1 to about 1:5, to form pumpable fluid complex compositions for further processing.

A preferred composition and process comprises spraying the molten mixtures of (a) dry active/cyclodextrin complex and (b) the normally solid hydrophilic polyethylene glycol material onto a solid substrate surface, then letting the droplets solidify on said surface. Said droplets are readily dissolvable by water or other aqueous media such as body fluids (e.g., sweat, saliva, urine, menses, etc.) to release the active.

Said hydrophilic polyethylene glycol materials have the general formula RO—$(CH_2CH_2O)_n$—R wherein each R is a hydrogen radical, a $C_1$-$C_{22}$ alkyl or alkenyl radical, or mixtures of such radicals, and n is from about 13 to about 450 (average MW of from about 600 to about 20,000) with the percentage of polyethylene glycol preferably being more than about 50%. Preferred R groups include a hydrogen radical, $C_1$-$C_4$ alkyl radicals, or mixtures of such radicals. More preferred polyethylene glycol materials are the hydrophilic polyethylene glycols, poly(ethylene glycol) methyl ethers, or mixtures thereof, with average MW's of from about 600 to about 20,000 (n from about 13 to about 450), preferably from about 1,000 to about 9,000 (n from about 20 to about 200), more preferably from about 1,400 to about 4,500 (n from about 30 to about 100). The weight ratio of the complex to the polyethylene glycol material is from about 1:1 to about 1:5, preferably from about 1:2 to about 1:4.

Other preferred compositions and processes involve prilling molten mixtures of (a) dry active/cyclodextrin complex and normally solid hydrophilic polyethylene glycol material as described above by, e.g., spray drying, marumarizing, etc., into solid prills with particle sizes of from about 10 microns to about 1,000 microns, preferably from about 50 microns to about 600 microns. Said solid prills can then be used, e.g., either (a) attached to a solid substrate surface by distributing the prills on said surface, melting said prills, and then resolidifying to bind said prills to said surface or (b) placed in a water-insoluble, but porous, pouch or enclosure. These articles will readily release the active when treated with water or other aqueous media.

Another preferred composition and process comprises forming the complex in the presence of a limited amount of solvent, e.g., water, then without the solvent (water) being removed, the normally solid polyethylene glycol materials are admixed in molten form with the complex/water mixture to form a pumpable mixture that can be used directly to form solid compositions by mixing with molten materials, e.g., hydrophobic fabric softener materials, that would ordinarily not be compatible with complex/water mixture alone. The pumpable mixtures are especially useful in the preparation of the fabric conditioning articles on substrates disclosed in more detail hereinafter.

In the above composition and process which utilize a mixture of carrier and solvent to suspend the complex, the ratio of carrier to complex typically varies from about 0.5 to about 3, preferably from about 0.6 to about 2, and more preferably from about 0.75 to about 1. The ratio of solvent plus carrier to complex typically varies from about 1:1 to about 5:1, preferably from about 1:1 to about 3:1. Preferably there is more carrier than solvent, the solvent is water, and/or the carrier is polyethylene glycol or alkylated polyethylene glycol, preferably having a molecular weight of from about 600 to about 20,000, and more preferably from about 1,000 to about 9,000.

The process using a mixture of carrier and solvent is also desirable because removal of the solvent adds an additional step, or steps, and can result in loss of some active, e.g., perfume.

The polyalkylene glycol materials preferably do not have any hydrophobic end group that will displace the active from the cyclodextrin. The polyalkylene glycols can contain other monomers in the chains, but the level of other monomers should be kept low to avoid displacement of the active from the cyclodextrin complex. Surprisingly, the complexes are effectively dispersed in the above carrier (solvent) but are not destroyed, e.g., by the carrier displacing the complexed active, e.g., perfume. Solvents such as ethylene glycol, propylene glycol, ethanol, glycerine, and molten sorbitol can form pumpable slurries, but will at least partially dissolve the complexes and thereby release the active.

Once the complexes are dispersed in the carrier, the complexes can be applied directly to substrates by using the suspension of complex in the carrier to achieve good distribution. E.g., the perfume/cyclodextrin in the carrier can be sprayed and/or spread onto the desired surface. Propellants, or air under pressure, can be used to form a dispersion of the carrier and complex. The complexes can release some of the active (perfume) when exposed to water in the atmosphere, but, surprisingly, a large amount of active, even volatile perfume active, remains in the complexes attached to the surface.

When the carrier is used to enrobe and/or protect the complex and/or to attach the complex to a substrate, the carrier is preferably solid at normally encountered temperatures. Polypropylene glycols are not solids so they will normally be used only as part of a mixture of carriers. Whether a specific carrier or mixture of carriers is solid can be readily determined by inspection.

One example of the use of the carrier/complex is in the preparation of a fabric conditioning product for use in a laundry dryer to treat laundered fabrics while they are being dried. When the product is then used to treat fabric, and the fabric is subsequently rewetted, perfume is released to provide an odor effect. Such odor effects are highly desirable both to generate pleasant odors when the fabric is rewetted, e.g., for towels and/or washcloths, and to cover undesirable odors such as those associated with perspiration. The odor effects on rewetting also serve as an effective pleasant signal that the fabric is becoming soiled while providing pleasant freshness effects until the soiled fabric can be exchanged for clean fabric. Thus it is essential that at least an effective amount of the complex be attached to the fabric. Effective amounts are typically in the range of from about 0.005 g to about 5 g, preferably from about 0.01 g to about 1 g, more preferably from about 0.05 g to about 0.5 g per kg of fabric. The wetter the fabric, the more perfume is released initially, and more of the remaining complex is effectively attached to the fabric. When the fabric is almost dry, little complex is destroyed and less perfume is applied initially, but the fabric exhibits odor effects upon rewetting.

The perfume/cyclodextrin complex can also be provided as part of a dryer-activated, fabric conditioning composition as described hereinafter. Such compositions provide a convenient way to introduce the perfume/cyclodextrin complex into the dryer. To prepare the such dryer activated fabric conditioning compositions, the complex is suspended in the carrier in an effective amount and applied to a substrate, either alone, or after being mixed with one or more of the fabric conditioning ingredients. For dryer activated compositions, the carrier should preferably be compatible with all kinds of dryer drum coatings. Such carriers typically do not have large amounts of terminal polyethylene glycol moieties.

6. SUBSTRATES

The substrates useful herein can be any solid material that can carry and release the active as needed. They comprise, for example, solid particulates including solid absorbent particulates, paper, woven fabrics, nonwoven fabrics, natural fibers, synthetic fibers, polymeric films including formed polymeric films, formed polymeric particles, or mixtures thereof. Cellulosic solids are especially desirable as natural biodegradable substrates. Preferred substrates are solid particulates, woven and nonwoven fabrics, films, and papers.

Desirable absorbent paper substrates are disclosed in U.S. Pat. Nos.: 3,905,863, Ayers, issued Sep. 16, 1975; 3,974,025, Ayers, issued Aug. 10, 1976; 4,191,609, Trokhan, issued Mar. 4, 1980; 4,440,597, Wells et al., issued Apr. 3, 1984; 4,529,480, Trokhan, issued Jul. 16, 1985; and 4,637,859, Trokhan, issued Jan. 20, 1987, all of said patents being incorporated herein by reference.

7. THE FABRIC CONDITIONING COMPOSITIONS

The present invention also relates to the preparation of improved solid, dryer-activated, fabric conditioning compositions and articles of manufacture in which the fabric conditioning compositions are, e.g., on a substrate.

A. Substrate Articles

In preferred embodiments, the present invention encompasses articles of manufacture, adapted for use to provide unique perfume benefits and to soften fabrics in an automatic laundry dryer, of the types disclosed in U.S. Pat. Nos: 3,989,631 Marsan, issued Nov. 2, 1976; 4,055,248, Marsan, issued Oct. 25, 1977; 4,073,996, Bedenk et al., issued Feb. 14, 1978; 4,022,938, Zaki et al., issued May 10, 1977; 4,764,289, Trinh, issued Aug. 16, 1988; 4,808,086, Evans et al., issued Feb. 28,1989; 4,103,047, Zaki et al., issued Jul. 25, 1978; 3,736,668, Dillarstone, issued Jun. 5, 1973; 3,701,202,° Compa et al., issued Oct. 31,1972; 3,634,947, Furgal, issued Jan. 18, 1972; 3,633,538, Hoeflin, issued Jan. 11, 1972; and 3,435,537, Rumsey, issued Apr. 1, 1969; and 4,000,340, Murphy et al., issued Dec. 28, 1976, all of said patents being incorporated herein by reference.

Typical articles of manufacture of this type include articles comprising:

I. a fabric conditioning composition comprising:
  i. from about 30% to about 99% of fabric softening agent; and
  ii. an effective amount, preferably from about 0.5% to about 70%, of a suspension of perfume/cyclodextrin complex in a suitable carrier as described hereinbefore, either alone, or in admixture with a solvent such as water:
II. a dispensing means which provides for release of an effective amount of said composition to fabrics in an automatic laundry dryer at automatic laundry dryer operating temperatures, e.g., from about 35° C. to 115° C.

When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1. The invention comprises the method of manufacturing such an article of manufacture utilizing said complex suspension ii. by premixing the complex with the carrier, and optional solvent, in an amount of complex, based on the total of carrier plus complex, of from about 0.5% to about 70%, preferably from about 5% to about 50%. The complex should be present in an amount sufficient to provide the desired benefit. The carrier is preferably solid at normal temperatures. However, liquid carriers can also be used to distribute the complex in, e.g., the softener and that will also provide protection.

The term "fabric softening agent" as used herein includes cationic and nonionic fabric softeners used alone and also in combination with each other. A preferred fabric softening agent of the present invention is a mixture of cationic and nonionic fabric softeners.

(1) Fabric Softening Agents

Examples of fabric softening agents that are especially useful in the substrate articles are the compositions described in U.S. Pat. Nos.: 4,103,047, Zaki et al., issued Jul. 25, 1978; 4,237,155, Kardouche, issued Dec. 2, 1980; 3,686,025, Morton, issued Aug. 22, 1972; 3,849,435, Diery et al., issued Nov. 19, 1974; and U.S. Pat. No. 4,073,996, Bedenk, issued Feb. 14, 1978; said patents are hereby incorporated herein by reference. Other fabric softening agents are disclosed hereinafter with respect to detergent-compatible fabric conditioning compositions.

Particularly preferred cationic fabric softeners for substrate articles include quaternary ammonium salts such as dialkyl dimethylammonium chlorides, methylsulfates and ethylsulfates wherein the alkyl groups can be the same or different and contain from about 14 to about 22 carbon atoms. Examples of such preferred materials include ditallowalkyldimethylammonium methylsulfate (DTDMAMS), distearyldimethylammonium methylsulfate, dipalmityldimethylammonium methylsulfate and dibehenyldimethylammonium methylsulfate. Also particularly preferred are the carboxylic acid salts of tertiary alkylamines disclosed in said Kardouche patent. Examples include stearyldimethylammonium stearate, distearylmethylammonium myristate, stearyldimethylammonium palmitate, distearylmethylammonium palmitate, and distearylmethylammonium laurate. These carboxylic salts can be made in situ by mixing the corresponding amine and carboxylic acid in the molten fabric conditioning composition.

Another preferred type of fabric softener is described in detail in U.S. Pat. No. 4,661,269, Toan Trinh, Errol H. Wahl, Donald M. Swartley and Ronald L. Hemingway, issued Apr. 28, 1987, said patent being incorporated herein by reference.

Examples of nonionic fabric softeners are the sorbitan esters, $C_{12}-C_{26}$ fatty alcohols, and fatty amines described herein.

A preferred fabric softening agent for use in substrate articles comprises a mixture of (1) $C_{10}-C_{26}$ acyl sorbitan esters and mixtures thereof, (2) quaternary ammonium salt, and (3) tertiary alkylamine. The quaternary ammonium salt is preferably present at a level of from about 5% to about 25%, more preferably from about 7% to about 20% of the fabric conditioning composition. The sorbitan ester is preferably present at a level of from about 10% to about 50%, more preferably from about 20% to about 40%, by weight of the fabric conditioning composition. The tertiary alkylamine is present at a level of from about 5% to about 25%, more preferably from 7% to about 20% by weight of the fabric conditioning composition. The preferred sorbitan ester comprises a member selected from the group consisting of $C_{10}-C_{26}$ acyl sorbitan monoesters and $C_{10}-C_{26}$ acyl sorbitan di-esters, and ethoxylates of said esters wherein one or more of the unesterified hydroxyl groups in said esters contain from 1 to about 6 oxyethylene units, and mixtures thereof. The quaternary ammonium salt is preferably in the methylsulfate form. The preferred tertiary alkylamine is selected from the group consisting of alkyldimethylamine and dialkylmethylamine and mixtures thereof, wherein the alkyl groups can be the same or different and contain from about 14 to about 22 carbon atoms.

Yet another preferred fabric softening agent comprises a carboxylic acid salt of a tertiary alkylamine, in combination with a fatty alcohol and a quaternary ammonium salt. The carboxylic acid salt of a tertiary amine is used in the fabric conditioning composition preferably at a level of from about 5% to about 50%, and more preferably, from about 15% to about 35%, by weight of the fabric treatment composition. The quaternary ammonium salt is used preferably at a level of from about 5% to about 25%, and more preferably, from about 7% to about 20%, by weight of the fabric treatment composition. The fatty alcohol can be used preferably at a level of from about 10% to about 25%, and more preferably from about 10% to about 20%, by weight of the fabric treatment composition. The preferred quaternary ammonium salt is selected from the group consisting of dialkyl dimethylammonium salt wherein the alkyl groups can be the same or different and contain from about 14 to about 22 carbon atoms and wherein the counteranion is selected from the group consisting of chloride, methylsulfate and ethylsulfate, preferably methylsulfate. The preferred carboxylic acid salt of a tertiary alkylamine is selected from the group consisting of fatty acid salts of alkyldimethylamines wherein the alkyl group contains from about 14 to about 22 carbon atoms, and the fatty acid contains from about 14 to about 22 carbon atoms, and mixtures thereof. The preferred fatty alcohol contains from about 14 to about 22 carbon atoms.

More biodegradable fabric softener compounds can be desirable. Biodegradability can be increased, e.g., by incorporating easily destroyed linkages into hydrophobic groups. Such linkages include ester linkages, amide linkages, and linkages containing unsaturation and/or hydroxy groups. Examples of such fabric softeners can be found in U.S. Pat. Nos.: 3,408,361, Mannheimer, issued Oct. 29, 1968; 4,709,045, Kubo et al., issued Nov. 24, 1987; 4,233,451, Pracht et al., issued Nov. 11, 1980; 4,127,489, Pracht et al., issued Nov. 28, 1979; 3,689,424, Berg et al., issued Sep. 5, 1972; 4,128,485, Baumann et al., issued Dec. 5, 1978; 4,161,604, Elster et al., issued Jul. 17, 1979; 4,189,593, Wechsler et al., issued Feb. 19, 1980; and 4,339,391, Hoffman et al., issued Jul. 13, 1982, said patents being incorporated herein by reference.

A preferred article of the present invention includes a fabric treatment composition which comprises from about 0.5% to about 70%, preferably from about 1% to about 60%, more preferably from about 5% to about 50%, of dispersion of perfume/cyclodextrin complex in a carrier, and from about 30% to about 99%, preferably from about 40% to about 90%, of fabric conditioning (softening) agent. The perfume is present at a level of from about 0.02% to about 6%, preferably from about 0.1% to about 5%, more preferably from about 1% to about 5%. Preferably, said fabric softening agent is selected from cationic and nonionic fabric softeners and mixtures thereof. Preferably, said fabric softening agent comprises a mixture of about 5% to about 80% of a cationic fabric softener and about 10% to about 85% of a nonionic fabric softener by weight of said fabric treatment composition. The carrier should be compatible with the rest of the composition. The selection of the components is such that the resulting fabric treatment composition has a melting point above about 38° C. and is flowable at dryer operating temperatures.

It is desirable, for ease of application, to intimately admix the ingredients of the fabric treatment before use and before application to a substrate dispensing means. This can be accomplished more readily by suspending/dissolving the complex in the carrier in accordance with this invention before premixing the complex with the other ingredients. For processing reasons, it is desirable to have a clay in the fabric softener composition in accordance with the teachings found in the patents incorporated by reference hereinbefore, and especially U.S. Pat. No. 4,073,996. As discussed hereinafter, clay provides special benefits in the context of the present invention.

(2) Dispensing Means

In the preferred substrate article embodiment, the fabric treatment compositions are provided as an article of manufacture in combination with a dispensing means such as a flexible substrate which effectively releases the composition in an automatic laundry (clothes) dryer. Such dispensing means can be designed for single usage or for multiple uses. The dispensing means can also be a "vanishing substrate material" that releases the fabric softener composition and then is dispersed and/or exhausted from the dryer.

The dispensing means will normally carry an effective amount of fabric treatment composition. Such effective amount typically provides sufficient fabric conditioning agent and/or anionic polymeric soil release agent for at least one treatment of a minimum load in an automatic laundry dryer. Amounts of fabric treatment composition for multiple uses, e.g., up to about 30, can be used. Typical amounts for a single article can vary from about 0.25 g to about 100 g, preferably from about 0.5 g to about 10 g, most preferably from about 1 g to about 5 g.

One such article comprises a sponge material releasably enclosing enough fabric treatment composition to effectively impart fabric soil release and softness benefits during several cycles of clothes. This multi-use article can be made by filling a hollow sponge with about 20 grams of the fabric treatment composition.

Other devices and articles suitable for dispensing the fabric treatment composition into automatic dryers include those described in U.S. Pat. Nos.: 4,103,047, Zaki et al., issued Jul. 25, 1978; 3,736,668, Dillarstone, issued Jun. 5, 1973; 3,701,202, Compa et al., issued Oct. 31, 1972; 3,634,947, Furgal, issued Jan. 18, 1972; 3,633,538, Hoeflin, issued Jan. 11, 1972; and 3,435,537, Rumsey, issued Apr. 1, 1969. All of these patents are incorporated herein by reference.

A highly preferred article herein comprises the fabric treatment composition releasably affixed to a flexible substrate in a sheet configuration. Highly preferred paper, woven or nonwoven "absorbent" substrates useful herein are fully disclosed in U.S. Pat. No. 3,686,025, Morton, issued Aug. 22, 1972, incorporated herein by reference. It is known that most substances are able to absorb a liquid substance to some degree; however, the term "absorbent" as used herein, is intended to mean a substance with an absorbent capacity (i.e., a parameter representing a substrate's ability to take up and retain a liquid) from about 4 to about 12, preferably from about 5 to about 7, times its weight of water.

Determination of absorbent capacity values is made by using the capacity testing procedures described in U.S. Federal Specifications UU-T-595b, modified as follows:
1. tap water is used instead of distilled water;
2. the specimen is immersed for 30 seconds instead of 3 minutes;
3. draining time is 15 seconds instead of 1 minute; and
4. the specimen is immediately weighed on a torsion balance having a pan with turned-up edges.

Absorbent capacity values are then calculated in accordance with the formula given in said Specification. Based on this test, one-ply, dense bleached paper (e.g., kraft or bond having a basis weight of about 32 pounds per 3,000 square feet) has an absorbent capacity of 3.5 to 4, commercially available household one-ply toweling paper has a value of 5 to 6; and commercially available two-ply household toweling paper has a value of 7 to about 9.5.

Using a substrate with an absorbent capacity of less than 4 tends to cause too rapid release of the fabric treatment composition from the substrate resulting in several disadvantages, one of which is uneven conditioning of the fabrics. Using a substrate with an absorbent capacity over 12 is undesirable, inasmuch as too little of the fabric treatment composition is released to condition the fabrics in optimal fashion during a normal drying cycle.

Such a substrate comprises a nonwoven cloth having an absorbent capacity of preferably from about 5 to 7 and wherein the weight ratio of fabric treatment composition to substrate on a dry weight basis ranges from about 5:1 to 1:1.

Nonwoven cloth substrates preferably comprise cellulosic fibers having a length of from 3/16 inch to 2 inches and a denier of from 1.5 to 5 and the substrates are adhesively bonded together with binder resin.

The flexible substrate preferably has openings sufficient in size and number to reduce restriction by said article of the flow of air through an automatic laundry dryer. The better openings comprise a plurality of rectilinear slits extended along one dimension of the substrate.

(3) Usage

The substrate embodiment of this invention can be used for imparting the above-described fabric treatment composition to fabric to provide perfume effects and/or softening and/or antistatic effects to fabric in an automatic laundry dryer in a process comprising: commingling pieces of damp fabric by tumbling said fabric under heat in an automatic clothes dryer with an effective amount of the fabric treatment composition, at least the continuous phase of said composition having a melting point greater than about 35° C. and said composition being mobilized, e.g., flowable, at dryer operating temperature, said composition comprising from about 0.5% to about 70%, preferably from about 1% to about 60%, more preferably from about 5% to about 50%, of a dispersion of perfume/cyclodextrin complex in a carrier, and from about 30% to about 99%, preferably from about 40% to about 90%, of fabric softening agent selected from the above-defined cationic and nonionic fabric softeners and mixtures thereof.

The method herein is carried out in the following manner. Damp fabrics, usually containing from about 1 to about 3.5 times their weight of water, are placed in the drum of an automatic laundry (clothes) dryer. In practice, such damp fabrics are commonly obtained by laundering, rinsing and spin-drying the fabrics in a standard washing machine. In a preferred mode, the present process is carried out by fashioning an article comprising the substrate-like dispensing means of the type hereinabove described in releasable combination with a fabric treatment composition. This article is simply added to a clothes dryer together with the damp fabrics to be treated. The dryer is then operated in standard fashion to dry the fabrics, usually at a temperature of from about 50° C. to about 80° C. for a period from about 10 minutes to about 60 minutes, depending on the fabric load and type. On removal from the dryer, the dried fabrics have acquired improved perfume benefits and are softened.

After one treatment in an automatic clothes dryer with an article of the present invention, the fabrics will have acquired a noticeable perfume benefit. I.e., more perfume is deposited in the form of perfume/cyclodextrin complex and, when the fabrics are rewetted, they will exhibit noticeable perfume odor.

(4) Viscosity Control Agents

Very useful ingredients are viscosity control agents, especially particulate clays, which are especially useful in the substrate articles. Examples of the particulate clays useful in the present invention are described in U.S. Pat. No. 4,103,047, supra, which is incorporated herein by reference. A preferred clay viscosity control agent is calcium bentonite clay, available from Southern Clay Products under the trade name Bentolite® L. The clay viscosity control agent is preferably present at a level of from about 0.5% to about 15%, more preferably from about 1.5% to about 10% by weight of the fabric conditioning composition.

The complexes can be protected during, e.g., the preparation of the substrate articles described hereinbefore by the use of the preferred clay viscosity control materials described hereinbefore. The complexes are especially vulnerable to the effect of nonionic surfactants, fatty ($C_{8-22}$) acid esters, fatty acids, fatty alcohols, etc. If the clay is not present, some of the perfume is displaced from the complex by ingredients in the softener. However, if the clay is present, the integrity of the complex is maintained. Since both the perfume/CD complex and the clay affect (increase) the viscosity and/or the yield point of the molten fabric conditioning composition, the amount of clay required for viscosity reasons is less with the presence of more complex. However, at least a certain amount of clay should be present, e.g., at least about 2%, preferably at least about 5% by weight of the complex, to provide protection of the perfume from displacement out of the complex by fabric softener and/or conditioning composition ingredients.

(5) Optional Ingredients

Well known optional components included in the fabric conditioning composition which are useful in the present invention are narrated in U.S. Pat. No. 4,103,047, Zaki et al., issued Jul. 25, 1978, for "Fabric Treatment Compositions," incorporated herein by reference.

(a) Uncomplexed (Free) Perfume

A preferred optional ingredient is free perfume, other than the perfume which is present as the perfume/cyclodextrin complex, which is also very useful for imparting odor benefits, especially in the product and/or in the dryer. Preferably, such uncomplexed perfume contains at least about 1%, more preferably at least about 10% by weight of said uncomplexed perfume, of substantive perfume materials. Such uncomplexed perfume is preferably present at a level of from about 0.10% to about 10% by weight of the portion of the composition that is transferred to the fabrics, e.g., everything but the dispensing means in substrate articles.

(b) Polymeric Soil Release Agents

Especially desirable optional ingredients are polymeric soil release agents, preferably those comprising block copolymers of polyalkylene terephthalate and polyoxyethylene terephthalate, and block copolymers of polyalkylene terephthalate and polyethylene glycol. Preferably, these polymeric soil release agents contain one, or more, negatively charged functional groups such as the sulfonate functional group, preferably as capping groups at the terminal ends of said polymeric soil release agent. The soil release agent is preferably present at a level of from about 1% to about 70%, more preferably from about 10% to about 60%, and most preferably from about 15% to about 50%, by weight of the fabric conditioning composition.

The polymeric soil release agents, including nonionic, etc., agents, preferably become molten at temperatures no higher than about 90° C. and have viscosities above about 10,000 cps at 85° C. Other polymeric soil release agents with higher melting points can be used when they dissolve in a viscosity reducing agent, especially those viscosity reducing agents which can act as solvents for the polymeric soil release agent.

The preferred polymeric soil release agents useful in the present invention include anionic polymeric soil release agents (ASRP's). Anionic polymeric soil release agents are compatible with the cationic softener agents of this invention and they are effective. Suitable anionic polymeric or oligomeric soil release agents are disclosed in U.S. Pat. No. 4,018,569, Trinh, Gosselink and Rattinger, issued Apr. 4, 1989, said patent being incorporated herein by reference.

The anionic soil release agent is preferably present at a level of from about 1% to about 70%, more preferably from about 10% to about 60%, and most preferably from about 15% to about 50%, by weight of fabric conditioning composition.

Other suitable polymers are disclosed in U.S. Pat. Nos.: 4,711,730, Gosselink and Diehl, issued Dec. 8, 1987; 4,808,086, Evans, Huntington, Stewart, Wolf, and Zimmerer, issued Feb. 24, 1989; and 4,702,857 Gosselink, issued Oct. 27, 1987, all of said patents being incorporated herein by reference.

B. Detergent-Compatible Compositions

Another type of fabric conditioning composition useful herein is detergent-compatible and includes compositions containing softening particles such as those known in the art, including specifically: U.S. Pat. No. 3,936,537, Baskerville, Jr., issued Feb. 3, 1976, and U.S. Pat. No. 4,095,946, Jones, issued Jun. 20, 1978, both of which teach the use of intimate mixtures of organic dispersion inhibitors (e.g., stearyl alcohol and fatty sorbitan esters) with solid fabric softener to improve the survival of the softener in the presence of detergent in the washer so that the softener can act on the fabrics when it is mobilized in the dryer, and U.S. Pat. No. 4,234,627, Schilling, issued Nov. 18, 1980, which teaches microencapsulation of fabric softener (The microcapsules survive the wash and adhere to the fabric surface. They are then ruptured by subsequent tumbling of the fabric in the dryer, thereby releasing softener to the fabrics.)

The particles in such detergent-compatible fabric conditioning compositions comprise at least about 10% of fabric softening agent, preferably cationic fabric softening agent. For detergent compatibility, the particles often have a coating as described hereinafter, a sufficiently large particle size (e.g., a minimum dimension greater than about 5,000 microns), or some combination of coating and particle size depending upon the identity of the softener, the other materials in the fabric softening composition, etc.

Typical cationic fabric softeners useful in the detergent-compatible fabric conditioning compositions herein include those that have been described hereinbefore with respect to the substrate articles.

Additional disclosure of materials which can be applied to fabrics along with cationic fabric softening agents in a laundry dryer and, therefore, can be part of the core composition of the particles herein, are disclosed in U.S. Pat. Nos.: 4,073,996, Bedenk et al., issued Feb. 14, 1978; 4,237,155, Kardouche, issued Dec. 2, 1980; and 4,421,792, Rudy et al., issued Dec. 20, 1983, all incorporated herein by reference.

The coating materials are disclosed in U.S. Pat. No. 4,898,680, Wierenga, Clauss, Culver and Piatt, issued Feb. 6, 1990.

A detailed listing of suitable surfactants and detergent builders for the detergent compositions herein can be found in U.S. Pat. No. 3,936,537, Baskerville, issued Feb. 3, 1976, incorporated by reference herein. Commercial sources of such surfactants can be found in McCutcheon's EMULSIFIERS AND DETERGENTS, North American Edition, 1984, McCutcheon Division, MC Publishing Company, also incorporated herein be reference.

The particles can be added to the wash solution in a sealed, porous water-insoluble pouch such as the type described in U.S. Pat. No. 4,223,029, Mahler et al., issued Sep. 16, 1980, incorporated by reference herein.

Preferred pouch structures are multi-pouch porous sheet structures such as described in U.S. Pat. Nos. 4,638,907, Bedenk and Harden, issued Jan. 27, 1987; and 4,259,383, Eggensperger et al., issued Mar. 31, 1981, both incorporated herein by reference. In a single pouch structure, the particles tend to collect in a relatively small area of the structure, whereas in a multi-pouch sheet structure the softener particles are distributed over a larger area of the structure thereby facilitating more even transfer of softener to fabrics in the dryer.

Suitable pouch materials include, paper, nonwoven synthetics such as spunbonded and wet laid polyester, and porous formed film plastic sheet material.

C. Compositional Advantages of Dryer-Activated Fabric Conditioners

Perfume delivery via the solid, dryer-activated fabric conditioning compositions of the invention in laundry fabric dryers is desirable in two ways. Product malodors can be covered by the addition of free perfume to the softener composition, and perfume can be transferred onto fabric with the softener actives in the laundry fabric dryer. Present technologies add perfume directly into the softener actives independent of the other softener components, or add the perfume in encapsulated form into the softener matrix. Encapsulated perfume can deposit on fabric and be retained for relatively long periods of time. However, most capsules that will survive processing are difficult to rupture, thus they may never release the perfume in a desirable way.

Addition of free perfume into the softener matrix allows the perfume to freely migrate creating an unstable condition and free perfume deposited on fabric dissipates fairly quickly when the fabrics are stored. If one wishes to have the perfume on fabric to last longer in storage or during wearing, it usually requires deposition of more perfume onto fabric in the laundry process. However, this often requires the product to have an undesirably high product odor and/or initial fabric odor.

The ability to have a product with low product perfume odor and an acceptable initial fabric perfume odor, but also have a long-lasting fabric perfume odor has been the goal of many development projects for consumer laundry products. The products of this invention preferably only contain enough free perfume to deliver both an acceptably low product perfume odor and an acceptable initial fabric perfume odor. Perfume incorporated into the product in the form of perfume/CD complex as part of a substrate article or in the form of solid fabric softener particles containing perfume/CD complex (in the case of detergent compatible products), will be released when the fabric is used in situations where renewed perfume odor is really and appropriately needed, e.g., when some moisture is present, such as when using wash cloths and towels in a bathroom, or when there is perspiration odor on clothes during and after a high level of physical activity.

The laundry products of this invention can also contain only the perfume/CD complex, without any noticeable amount of free perfume. In this case, the products function initially almost as unscented products. Fabrics treated with these products do not carry any obvious perfume odor that can "clash" with other expensive personal fragrances that the consumer may wish to wear. Only when extra perfume is needed, such as for bathroom use, or for perspiration, is the perfume in the complex released.

During storage of the treated fabric, a small amount of perfume can escape from the complex as a result of the equilibrium between the perfume/CD complex and free perfume and CD, and a light scent is obtained. If the product contains both free and complexed perfume, this escaped perfume from the complex contributes to the overall fabric perfume odor intensity, giving rise to a longer lasting fabric perfume odor impression.

Thus, by adjusting the levels of free perfume and perfume/CD complex it is possible to provide a wide range of unique perfume profiles in terms of timing and/or perfume identity. Solid, dryer-activated fabric conditioning compositions are a uniquely desirable way to apply the complexes, since they are applied at the very end of the fabric treatment regimen when the fabric is clean and when there are almost no additional treatments that can affect the perfume.

The perfume/cyclodextrin complexes are incorporated into the fabric conditioning compositions after being suspended in the carrier, especially when the compositions are to be added to laundry detergents. It is believed that when the perfume/cyclodextrin complexes are encapsulated in fabric softener, they are attached to the fabric in the laundry dryer.

The articles of manufacture disclosed hereinbefore can impart long-lasting perfume benefits plus softening and/or antistatic effects to fabrics when used in an automatic laundry dryer.

This invention also contributes to the aesthetics of the clothes washing process. One important point in the laundry process where the consumer appreciates the odor (fragrance) is during the wash process (i.e., from the wash water and during the transfer of wet clothes to the dryer). This aesthetic benefit is currently provided mainly by the perfume added via the detergent composition or liquid softener composition to the wash and/or rinse water. Clothes that have been pretreated, e.g., in the dryer with the articles of manufacture disclosed herein give off a burst of fragrance in the wash water, and the resulting fabrics are "perfumy" even though no other perfume is used in the washing, rinsing and/or drying steps.

8. OTHER SUBSTRATE ARTICLES

In addition to the fabric conditioning compositions, one can prepare articles of manufacture comprising cyclodextrin complexes of actives, e.g., perfume or flavor, attached to substrates by normally solid polyalkylene glycol. The complex/carrier mixture can be applied directly while molten by printing or as a spray, or as a powder which can then be attached to the substrate by melting the surface of the powder.

Such articles include absorbent articles such as paper towels, paper napkins, diapers, catamenial devices, and dress shields. A perfume complex can provide either a positive pleasant odor or a counter-active odor effect to either hide, or cancel out, the odor of body fluids when the articles are wetted. The complex/carrier composition provides a simple convenient way to prepare such articles and the carrier provides improved protection for the complex until the carrier is dissolved by the body fluids.

Other desirable articles of manufacture include flavor complexes attached to particulate substrates by the solid carrier. Such articles can be used as foods, drinks, etc., or can be incorporated into foods, drinks, etc., to provide improved flavor effects when contacted with aqueous liquids, either in the preparation of foods or in the mouth.

Other articles include pharmaceutical agents attached to substrates, preferably particulate substrates, for ease in dispensing. The solid carriers provide improved protection during storage.

In general, any active that will benefit from improved protection by the solid carrier and/or requires a dispersed form for maximum effectiveness, can benefit from this invention both in improved effectiveness and ease of preparation.

All percentages, ratios, and parts herein are by weight unless otherwise stated.

The following are nonlimiting examples of the instant articles and methods.

Two different perfumes used in the following Examples are as follows:

Perfume (A)

Perfume A is a substantive perfume which is composed mainly of moderate and nonvolatile perfume ingredients. The major ingredients of Perfume C are benzyl salicylate, para-tertiary-butyl cyclohexyl acetate, para-tertiary-butyl-alpha-methyl hydrocinnamic aldehyde, citronellol, coumarin, galaxolide, heliotropine, hexyl cinnamic aldehyde, 4-(4-hydroxy-4-methyl pentyl)-3-cyclohexene-10-carboxaldehyde, methyl cedrylone, gamma-methyl ionone, and patchouli alcohol.

Perfume (B) (More Volatile Portion of Perfume A)

Perfume B is a rather nonsubstantive perfume which is composed mainly of highly and moderately volatile fractions of Perfume A. The major ingredients of Perfume B are linalool, alpha terpineol, citronellol, linalyl acetate, geraniol, hydroxycitronellal, terpinyl acetate, eugenol, and flor acetate.

The above-defined perfumes and others, as defined hereinafter, are used to form the following complexes, which are used in the Examples herein.

COMPLEX 1

Perfume B/$\beta$-Cyclodextrin

A mobile slurry is prepared by mixing about 1 kg of $\beta$-CD and 1,000 ml of water in a stainless steel mixing bowl of a KitchenAid mixer using a plastic coated heavy-duty mixing blade. Mixing is continued while about 176 g of Perfume B is slowly added. The liquid-like slurry immediately starts to thicken and becomes a creamy paste. Stirring is continued for about 30 minutes. The paste is now dough-like in appearance. About 500 ml of water is added to the paste and blended well. Stirring is then resumed for an additional approximately 30 minutes. During this time the complex again thickens, although not to the same degree as before the additional water is added. The resulting creamy complex is spread in a thin layer on a tray and allowed to air dry. This produces about 1100 g of granular solid which is ground to a fine power. The complex retains some free perfume and still has a residual perfume odor.

COMPLEX 2

The last traces of water in Complex 1 are removed by freeze drying, after which Complex 1 loses about 1% of its weight. The resulting solid is washed with diethyl ether to remove the residual uncomplexed perfume. The last traces of ether are removed in vacuo to give Complex 2 as a white powder which is practically odorless when dry but produces the fragrance of Perfume B when added to water.

Procedure for Determination of Complex Stability and Mixture Flowability/Pumoability The suitability of a carrier (mobile phase) material is determined by two criteria: (1) compatibility with the complex, i.e., not decomposing the complex, and (2) flowability or pumpability of the resulting mixture. In the following Examples 1 to 17, and Comparative Examples 18 to 22, the carriers are evaluated by admixing the indicated complexes as follows.

The washed Complex 2 is mixed with the indicated carriers (solvents or meltable solids having melting temperature or liquid/solid phase transition temperature at about or below 100° C.). Two parts of the complex powder and 3 parts of the carrier are mixed together until they are blended well.

The stability of the complex in the carrier dispersion is determined by the relative presence, or absence, of the perfume odor from the resulting mixture. The resulting liquid mixture is considered stable if no perfume odor, or only very slight perfume odor, is noticed. If the perfume odor is evident and strong, the mixture is considered unstable and thus not suitable. Suitable flowability/pumpability is determined by pourability. I.e., the container is tiled to see whether the mixture can flow. The mixture is considered flowable and pumpable if the mixture can run down the wall of the container.

Nonlimiting Examples of suitable carriers in which the complex is stable (Examples 1 to 21) and Examples of nonsuitable materials in which the complex is unstable (Comparative Examples A to E), and the respective compatibility and stability observations are summarized in Table 1.

TABLE 1

| Exs. | Carriers | Pourability | Complex Stability |
|---|---|---|---|
| 1 | Polyethylene glycol, avg. MW 600 | Viscous but pourable | Little perfume odor |
| 2 | Polyethylene glycol, avg. MW 1,500 | Viscous but pourable when molten | Almost no perfume odor |
| 3 | Polypropylene glycol, avg. MW 400 | Pourable | Slight perfume odor |
| 4 | Polypropylene glycol, avg. MW 2,000 | Pourable | No perfume odor |
| 5 | $C_2H_5OCH_2CH_2OCH_2CH_2OH$ | Pourable | No perfume odor |
| 6 | $CH_3OCH_2CH_2OCH_2CH_2OH$ | Pourable | Slight perfume odor |
| 7 | $C_4H_9OCH_2CH_2OCH_2CH_2OH$ | Pourable | No perfume odor |
| 8 | $CH_3OCH_2CH_2OCH_2CH_2OCH_2CH_2OH$ | Pourable | No perfume odor |

TABLE 1-continued

| | | Pourability | Complex Stability |
|---|---|---|---|
| 9 | CH$_3$CH$_2$OCH$_2$CH$_2$OCH$_2$CH$_2$OCH$_2$CH$_2$OH | Pourable | No perfume odor |
| 10 | CH$_3$OCH$_2$CH(CH$_3$)OH | Pourable | No perfume odor |
| 11 | CH$_3$OCH$_2$CH(CH$_3$)OCH$_2$(CH$_3$)OH | Pourable | No perfume odor |
| 12 | Poly(ethylene glycol) methyl ether, avg. MW 2,000 | Viscous but pourable when molten | Almost no perfume odor |
| 13 | Pluronic L-81 | Viscous but pourable | Very slight perfume |
| 14 | Pluronic P-75 | Viscous but pourable when molten | No perfume odor |
| 15 | Pluronic F-38 | Viscous but pourable when molten | Very slight perfume odor |
| 16 | Pluronic R 17R1 | Viscous but pourable | No perfume odor |
| 17 | Pluronic R 17R4 | Viscous but pourable | No perfume odor |
| 18 | Pluronic R 31R1 | Viscous but pourable | No perfume odor |
| 19 | Tetronic 1102 | Viscous but pourable | No perfume odor |
| 20 | Tetronic 707 | Viscous but pourable when molten | Very slight perfume odor |
| 21 | Diethoxylated-ethyltallow ammonium ethylsulfate (Varstat 66) | Viscous but pourable | No perfume odor |
| Comp. Exs. | Mobile Phase | | |
| A | Ethylene glycol | Viscous but pourable | Strong perfume odor |
| B | Diethylene glycol | Viscous but pourable | Perfume odor evident |
| C | 1,2-Propanediol | Pourable | Perfume odor evident |
| D | Glycerine | Barely pourable | Strong perfume odor |
| E | d-Sorbitol | Very stiff paste when molten, barely pourable | Strong perfume odor |

EXAMPLE 1

Two parts of Complex 2 are mixed thoroughly with about 3 parts of molten polyethylene glycol, with average MW of about 600, at about 70° C. The liquid mixture is viscous, but can run down the wall of the container, indicating that the mixture is pourable. Only a faint odor of perfume is noticed, indicating that Complex 2 is stable in this carrier.

EXAMPLE 2

The procedure and results are similar to those of Example 1, except that molten polyethylene glycol with average MW of about 1,450 is used.

EXAMPLES 3-11

The procedures and results are similar to those of Example 1, except that Complex 2 is mixed with each liquid carrier at room temperature.

EXAMPLE 12

The procedure and results are similar to those of Example 1, except that poly(ethylene glycol) methyl ether with average MW of about 2,000 is used as the carrier. The mixture is viscous, but pourable, at about 70° C.

EXAMPLE 13

The procedure and results are similar to those of Example 1, except that Pluronic L-81 is used as the carrier at room temperature. The Pluronic L-81 has the following formula

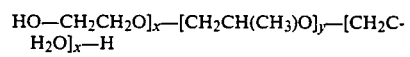

and has an average MW of about 2,750, with the MW of the [CH$_2$CH(CH$_3$)O]$_y$ portion being about 2,475 (y being about 43) and the total MW of the [CH$_2$CH$_2$O]$_x$ portions being about 275 (total x being about 6). The mixture is viscous, but pourable, at room temperature, and Complex 2 is stable in the mixture.

EXAMPLE 14

The procedure and results are similar to those of Example 13, except that Pluronic P-75 is used as the carrier at about 70° C. This Pluronic P-75 has an average MW of about 4,150, with y being about 36 and total x being about 47.

EXAMPLE 15

The procedure and results are similar to those of Example 13, except that Pluronic P-38 is used as the carrier at about 70° C. This Pluronic P-75 has an average MW of about 4,700, with y being about 16 and total x being about 85.

EXAMPLE 16

The procedure and results are similar to those of Example 1, except that Pluronic R 17R1 is used as the carrier. The Pluronic 17R1 has the following formula HO—[CH(CH$_3$)CH$_2$O]$_y$—[CH$_2$CH$_2$O]$_x$—[CH$_2$CH(CH$_3$)O]$_y$—H with the total MW of the HO—[CH(CH$_3$)CH$_2$O] and [CH$_2$CH(CH$_3$)O] portions being about 1,700 (total y being about 28) and the MW of the [CH$_2$CH$_2$O] portion being about 190 (x being about 4.3). The mixture is viscous, but pourable, at room temperature, and Complex 2 is stable in the mixture.

EXAMPLE 17

The procedure and results are similar to those of Example 13, except that Pluronic R 17R4 is used as the carrier. This Pluronic R has a total y of about 28 and x of about 26.

EXAMPLE 18

The procedure and results are similar to those of Example 13, except that Pluronic R 31RI is used as the carrier. This Pluronic R has a total y of about 52 and x of about 8.

EXAMPLE 19

The procedure and results are similar to those of Example 16, except that Tetronic 1102 is used as the carrier at about 70° C. This Tetronic 1102 has an average MW of about 6,200, with total y being about 21 and total x being about 113.

EXAMPLE 20

The procedure and results are similar to those of Example 16, except that Tetronic 707 is used as the carrier at about 70° C. This Tetronic 707 has an average MW of about 12,200, with total y being about 63 and total x being about 194.

EXAMPLE 21

The procedure and results are similar to those of Example 13, except that Varstat 66 is used as the carrier.

COMPARATIVE EXAMPLES A–D

Similar procedures as in Examples 3–11 are used. In these Comparative Examples A–D, the mixture of liquid materials (ethylene glycol, diethylene glycol, 1,2-propanediol, and glycerine, respectively) with Complex 2 release strong perfume odor, indicating that these liquid materials decompose, at least partially, the complex, and thus are not suitable as carriers.

COMPARATIVE EXAMPLE E

Similar procedure as in Example 1 is used except that molten d-sorbitol at about 110° C. is used as the carrier. The mixture is barely pourable and releases strong perfume odor, thus d-sorbitol is not suitable as a carrier.

EXAMPLE 22

Similar procedure and results as in Example 2 are used except that about 1 part of Complex 2 is mixed with about 3 parts of molten polyethylene glycol with average MW of about 1,450 at about 70° C.

| Components | Example 23 | Example 24 |
|---|---|---|
| Octadecyldimethylamine | 9.55 | 8.67 |
| C$_{16}$-C$_{18}$ fatty acid | 16.88 | 15.32 |
| DTDMAMS | 16.54 | 15.01 |
| Sorbitan monostearate | 16.54 | 15.01 |
| Clay | 3.27 | 3.54 |
| Composition of Example 2 | 37.22 | — |
| Composition of Example 22 | — | 40.00 |
| Free Perfume A | — | 2.45 |
| Total | 100.00 | 100.00 |

EXAMPLE 23

A first blend of about 9.55 parts octadecyldimethylamine (Ethyl Corporation) and about 16.88 parts C$_{16-18}$ fatty acid (Emery Industries, Inc.) are melted together at 80° C., and a second blend of about 16.54 parts sorbitan monostearate (Mazer Chemicals, Inc.) and 16.54 parts ditallowdimethylammonium methylsulfate, DTDMAMS, (Sherex Chemical Co.) are melted together at about 80° C. The two blends are admixed to form the softener component of the composition, during which time the mixture is kept molten in a boiling water bath. The calcium bentonite clay (3.27 parts Bentolite L, available from Southern Clay Co.) is then slowly added to the mixture while high shear mixing. An amount of about 37.22 parts of the composition of Example 2 (comprising 14.89 parts of Complex 2 and 22.33 parts of polyethylene glycol with average MW of about 1,450) is then added, and the formula is mixed until the mixture is smooth and completely homogenous.

The coating mixture is applied to preweighed nonwoven substrate sheets of about 9 inch × 11 inch (approximately 23 cm × 28 cm) dimensions. The substrate sheets are comprised of about 70% 3-denier, approximately 1-9/16 inch (about 4 cm) long rayon fibers with about 30% polyvinyl acetate binder. The substrate weight is about 16 g per square yard (about 1.22 g/sheet). A small amount of formula is placed on a heated metal plate with a spatula and then is spread evenly with a wire metal rod. A nonwoven sheet is placed on the metal plate to absorb the coating mixture. The sheet is then removed from the heated metal plate and allowed to cool to room temperature so that the coating mix can solidify. The sheet is weighed to determine the amount of coating mixture on the sheet. The target coating is 3.33 g per sheet. Each sheet contains about 1.98 g of softener, about 0.11 g of clay, and about 1.24 g of the composition of Example 2 comprising about 0.50 g of Complex 2 and about 0.74 g of polyethylene glycol. If the weight is in excess of the target weight, the sheet is placed back on the heated metal plate to remelt the coating mixture and remove some of the excess. If the weight is under the target weight, the sheet is also placed on the heated metal plate and more coating mixture is added.

EXAMPLE 24

A dryer-added fabric conditioning article comprising a rayon nonwoven fabric substrate having a weight of 1.22 g per 99 sq. in. (approximately 639 cm$^2$)] and a fabric conditioning composition is prepared in the following manner.

A premixture is prepared by admixing about 8.67 parts octadecyldimethylamine with about 15.32 parts C$_{16}$-C$_{18}$ fatty acid at about 75° C. Another premixture is prepared by admixing about 15.01 parts sorbitan monostearate and about 15.01 parts ditallowdimethylammonium methylsulfate at about 75° C. The two premixtures are pumped into a mixing vessel with high shear mixing at about 75° C. After the addition is completed and a sufficient period of mixing time has elapsed, about 3.54 parts of Bentolite L particulate clay is added slowly while maintaining the high shear mixing action. Then about 40 parts of the composition of Example 22, molten at about 75° C., is pumped into the mixing vessel, with the high shear mixing action being maintained. Finally about 2.45 parts of free Perfume A is added to complete the preparation of the fabric conditioning composition.

A flexible substrate, comprised of about 70% 3-denier, 1-9/16 inch long (approximately 4 cm) rayon fibers and about 30% polyvinyl acetate binder, is impregnated by coating one side of a continuous length of the substrate and contacting it with a rotating cylindrical member which serves to press the liquified mixture into the interstices of the substrate. The amount of fabric conditioning mixture applied is controlled by the flow rate of the mixture and/or the line speed of the substrate. The substrate is passed over several chilled tension rolls which help solidify the conditioning mixture. The substrate sheet is 9 inches wide (approximately 23 cm) and is perforated in lines at 11 inch intervals (approximately 28 cm) to provide detachable sheets. Each sheet is cut with a set of knives to provide three evenly spaced parallel slits averaging about 4 inches in length (approximately 10 cm). In this Example 25, the application rate is adjusted to apply about 3.00 g of coating mixture per sheet. Each sheet contains about 1.62 g of softener, about 0.11 g of clay, about 1.20 g of the composition of Example 22, and about 0.074 g of free Perfume A.

Two laundry loads with similar garment compositions are washed with unscented TIDE ® detergent. The wet laundry loads are transferred to, and dried in, electric tumble dryers, with, respectively, fabric conditioning sheets of Examples 23 and 24. The resulting dry fabrics have low perfume odor, but when the fabrics are wetted, a noticeably stronger perfume odor is obtained.

In the following Examples 25-33, the use of a mixture of carrier and solvent (water) is used to suspend the complex. The advantages of this variation are described hereinbefore.

EXAMPLE 25

Perfume A/$\beta$-CD/PEG 3350 Composition

A mobile slurry is prepared by mixing about 336 g $\beta$-cyclodextrin and about 269 g deionized water (distilled water can be used) at about 25° C. in a stainless steel mixing bowl of a KitchenAid mixer using the flat beater mixing attachment. Mixing is continued while about 59 g of Perfume A is added rapidly. The low viscosity slurry immediately begins to thicken and becomes a stiff paste within a minute. Mixing is continued while 336 g of polyethylene glycol with average MW of about 3,350 at about 75° C. is slowly added. This final composition is mixed until homogeneous for about 15 minutes.

EXAMPLE 26

Perfume A/$\beta$-CD/Surfynol 465 Composition

A mobile slurry is prepared by mixing about 410 g $\beta$-cyclodextrin and about 330 g deionized water (distilled water can be used) at about 25° C. in a stainless steel mixing bowl of a KitchenAid mixer using the flat beater mixing attachment. Mixing is continued while about 73 g of Perfume A is added rapidly. The low viscosity slurry immediately begins to thicken and becomes a stiff paste within a minute. Mixing is continued while 187 g of Surfynol 465 (supplied by Air Products) at about 25° C. is slowly added. This final composition is mixed until homogeneous for about 15 minutes.

EXAMPLE 27

Perfume B/$\beta$-CD/PEG 3350 Composition

Perfume B/$\beta$-CD/PEG 3350 composition is prepared by the process of Example 25, using Perfume B instead of Perfume A.

EXAMPLE 28

Perfume B/$\beta$-CD/PEG 1450 Composition

Perfume B/$\beta$-CD/PEG 1450 composition is prepared by the process of Example 27, using polyethylene glycol with average MW of about 1,450 instead of MW of 3,350.

EXAMPLE 29

Perfume B/$\beta$-CD/PEG 8000 Composition

Perfume B/$\beta$-CD/PEG 8000 composition is prepared by the process of Example 27, using polyethylene glycol with average MW of about 8,000 instead of MW of 3,350.

In the following Examples 30-34, compositions of Examples 25-29 are used to facilitate incorporation of the complex into the product.

| Components | Compositions | |
|---|---|---|
| | Example 30 | Example 31 |
| Octadecyldimethylamine | 8.33 | 8.14 |
| $C_{16}$-$C_{18}$ Fatty Acid | 14.70 | 14.38 |
| Ditallowalkyldimethylammonium methylsulfate (DTDMAMS) | 14.41 | 14.10 |
| Sorbitan Monostearate | 14.41 | 14.10 |
| Clay | 2.55 | 2.55 |
| Composition of Example 25 | 45.60 | — |
| Composition of Example 29 | — | 45.60 |
| Free Perfume A | — | 1.13 |
| Totals | 100.00 | 100.00 |

| | Ex. 32 | Ex. 33 | Ex. 34 |
|---|---|---|---|
| Octadecyldimethylamine | 10.40 | 10.40 | 11.00 |
| $C_{16}$-$C_{18}$ Fatty Acid | 18.38 | 18.38 | 19.44 |
| Ditallowalkyldimethylammonium methylsulfate (DTDMAMS) | 17.99 | 17.99 | 19.03 |
| Sorbitan Monostearate | 17.99 | 17.99 | 19.03 |
| Clay | 3.60 | 3.60 | 3.80 |
| Composition of Example 28 | 30.06 | — | — |
| Composition of Example 27 | — | 30.06 | — |
| Composition of Example 26 | — | — | 26.03 |
| Free Perfume A | 1.58 | 1.58 | 1.67 |
| Totals | 100.00 | 100.00 | 100.00 |

PREPARATION OF EXAMPLES 30-33

EXAMPLE 30

A dryer-added fabric conditioning article of manufacture comprising a rayon nonwoven fabric substrate (having a weight of about 1.22 gram per 99 sq. in.) and a fabric conditioning composition having the above-mentioned composition is prepared in the following manner.

Preparation of the Fabric Treatment Mixture

A blend of about 8.33 parts of octadecyldimethylamine (Lonza Corp.) and about 14.70 parts of $C_{16}$-$C_{18}$ fatty acid (Lonza Corp.) is melted at about 80° C., and a blend of about 14.41 parts of DTDMAMS (Sherex Chemical Co.) and about 14.41 parts of sorbitan monostearate (Mazer Chemicals, Inc.) is melted at about 80° C. The two blends are then mixed together to form the molten, essentially hydrophobic, softener component.

Next, about 2.55 parts of calcium bentonite clay is added to the softener component and the resulting blend is homogenized with high-shear mixing. Then, about 45.60 parts of the composition of Example 25 is added at about 75° C., also with high-shear mixing, until a uniform blend results. The composition of Example 25 homogenizes with the softener mixture easily. When the polyethylene glycol is not present, the water/cyclodextrin mixture will not homogenize with the molten hydrophobic softener component.

Preparation of Fabric Conditioning Sheets

The fabric treatment mixture is applied to preweighed nonwoven substrate sheets of a 9 inch×11 inch (approximately 23 ×28 cm) dimension. The substrate sheets are comprised of about 70%, approximately 3-denier, 1-9/16 inch (approximately 4 cm) long rayon fibers with about 30% polyvinyl acetate binder. A small amount of the fabric treatment mixture is placed on a heated metal plate with a spatula and then is spread evenly with a small metal roller. A nonwoven sheet is placed on it to absorb the fabric treatment mixture. The sheet is then removed from the heated metal plate and allowed to cool to room temperature so that the fabric treatment mixture can solidify. The sheet is weighed to determine the amount of fabric treatment mixture on the sheet. The target coating amount is 3.86 g per sheet. Each sheet contains about 1.98 g of softener; about 1.78 g of the composition of Example 25 and about 0.10 g of clay.

If the weight is under the target weight, the sheet is placed on a heated metal plate and more fabric treatment mixture is added. If the weight is in excess of the target weight, the sheet is placed back on the heated metal plate to remelt the fabric treatment mixture and remove some of the excess.

EXAMPLE 31

A dryer-added fabric conditioning article comprising a rayon nonwoven fabric substrate [having a weight of 1.22 g per 99 sq. in. (approximately 639 cm$^2$)] and a fabric conditioning composition is prepared in the following manner.

A premixture is prepared by admixing about 8.14 parts octadecyldimethylamine with about 14.38 parts $C_{16}$-$C_{18}$ fatty acid at about 75° C. Another premixture is prepared by admixing about 14.10 parts sorbitan monostearate and about 14.10 parts ditallowdimethylammonium methylsulfate at about 75° C. The two premixtures are pumped into a mixing vessel with high shear mixing at about 75° C. After the addition is completed and a sufficient period of mixing time has elapsed, about 2.55 parts of Bentolite L particulate clay is added slowly while maintaining the high shear mixing action. Then about 45.60 parts of the composition of Example 29 is pumped into the mixing vessel, with the high shear mixing action being maintained. Finally about 1.13 parts of free Perfume A is added to complete the preparation of the fabric conditioning composition.

A flexible substrate, comprised of about 70% 3-denier, 1-9/16 inch long (approximately 4 cm) rayon fibers and about 30% polyvinyl acetate binder, is impregnated by coating one side of a continuous length of the substrate and contacting it with a rotating cylindrical member which serves to press the liquified mixture into the interstices of the substrate. The amount of fabric conditioning mixture applied is controlled by the flow rate of the mixture and/or the line speed of the substrate. The substrate is passed over several chilled tension rolls which help solidify the conditioning mixture. The substrate sheet is 9 inches wide (approximately 23 cm) and is perforated in lines at 11 inch intervals (approximately 28 cm) to provide detachable sheets. Each sheet is cut with a set of knives to provide three evenly spaced parallel slits averaging about 4 inches in length (approximately 10 cm). In this Example 31, the application rate is adjusted to apply about 3.90 g of coating mixture per sheet. Each sheet contains about 1.98 g of softener, about 0.10 g of clay, about 1.78 g of the composition of Example 29, and about 0.04 g of free Perfume A.

EXAMPLE 32

A dryer-added fabric conditioning article of manufacture comprising a rayon nonwoven fabric substrate (having a weight of about 1.22 gram per 99 sq. in.) and a fabric conditioning composition having the above-mentioned composition is prepared in the following manner.

Preparation of the Fabric Treatment Mixture

A blend of about 10.40 parts of octadecyldimethylamine (Lonza Corp.) and about 18.38 parts of $C_{16}$-$C_{18}$ fatty acid (Lonza Corp.) is melted at about 80° C., and a blend of about 17.99 parts of DTDMAMS (Sherex Chemical Co.) and about 17.99 parts of sorbitan monostearate (Mazer Chemicals, Inc.) is melted at about 80° C. The two blends are then mixed together to form the molten, essentially hydrophobic, softener component.

Next, about 3.60 parts of calcium bentonite clay is added to the softener component and the resulting blend is homogenized with high-shear mixing. Then, about 30.06 parts of the composition of Example 28 is added at about 75° C., also with high-shear mixing, until a uniform blend results. The composition of Example 28 homogenizes with the softener mixture easily. When the polyethylene glycol is not present, the water/cyclodextrin mixture will not homogenize with the molten softener component. Finally, 1.58 parts of free Perfume A is added with mixing.

A flexible substrate, comprised of about 70% 3-denier, 1-9/16 inch long (approximately 4 cm) rayon fibers and about 30% polyvinyl acetate binder, is impregnated by coating one side of a continuous length of the substrate and contacting it with a rotating cylindrical member which serves to press the liquified mixture into the interstices of the substrate. The amount of fabric conditioning mixture applied is controlled by the flow rate of the mixture and/or the line speed of the substrate. The substrate is passed over several chilled tension rolls which help solidify the conditioning mixture. The substrate sheet is 9 inches wide (approximately 23 cm) and is perforated in lines at 11 inch intervals (approximately 28 cm) to provide detachable sheets. Each sheet is cut with a set of knives to provide three evenly spaced parallel slits averaging about 4 inches in length (approximately 10 cm). In this Example 32, the application rate is adjusted to apply about 2.78 g of coating mixture per sheet. Each sheet contains about 1.80 g of softener, about 0.10 g of clay, about 0.84 g of the composition of Example 28, and about 0.04 g of Free Perfume A.

EXAMPLE 33

The coating mixture and fabric conditioning sheets of Example 33 are prepared similarly to that of Example 32, except that the composition of Example 27 is used instead of the composition of Example 28.

EXAMPLE 34

The coating mixture and fabric conditioning sheets of Example 34 are prepared similarly to that of Example 30, except that the composition of Example 26 is used at a target coating weight of about 2.63 grams per sheet.

Fabric Treatment

Five laundry loads with similar garment composition are washed in washers with unscented TIDE ® detergent. The wet laundry loads are transferred to, and dried in, electric tumble dryers, respectively, with fabric conditioning sheets of Examples 30–34.

The resulting dry fabrics have low perfume odor, but when the fabrics are wetted, a noticeably stronger perfume odor is obtained.

EXAMPLE 35

Solid Perfume Complex/PEG 1450 Particles

The molten composition of Example 22, kept at about 80° C. temperature, is atomized in a spray drying tower to obtain solid particles. Solid particles solidify on the wall of the tower and are removed for particle size classification. Some particles that have sizes larger than about 500 microns are ground further to reduce the particle size by cryogenic grinding with dry ice. The particles having sizes between about 100 microns and about 500 microns are used to make the perfumed paper towel of Example 37.

EXAMPLE 36

Solid Perfume Complex/PEG 8000 Particles

Solid particles of Perfume B complex in polyethylene glycol of average MW of about 8,000 are made similarly to those of Example 35, using polyethylene glycol of average MW of about 8,000.

EXAMPLE 37

A perfumed paper towel is made by distributing 20 mg of the solid particles of perfume complex in polyethylene glycol of Example 35 onto a sheet of BOUNTY ® paper towel of approximate dimensions 28 cm × 28 cm, then placing the paper towel in an 80° C. oven for 5 minutes to attach the particles onto the paper towel. The resulting dry paper towel has low perfume odor, but when it is wetted, a noticeably stronger perfume odor is obtained.

EXAMPLE 38

A disposable diaper is made by a process similar to that disclosed in Example VII of U.S. Pat. No. 4,610,678, Weisman et al, issued Sep. 9, 1986, said patent being incorporated herein by reference. The solid particles of perfume complex in the polyethylene glycol of Example 36 are attached to the top wet strength tissue paper by uniformly distributing about 0.25 g per sheet and heating to about 80° C. The resulting diaper has very low perfume odor, but releases a noticeable level of perfume odor when wetted.

EXAMPLE 39

One part of Complex 1 is uniformly mixed with 3 parts of molten polyethylene glycol with an average MW of about 1,450 at about 70° C.

EXAMPLE 40

A fabric freshening sheet is made by uniformly coating 23 cm × 28 cm nonwoven substrate sheets as described in Example 23 with 3.5 g of the composition of Example 39, by the procedure described in Example 23. The resulting sheets are added to freshly washed wet laundry loads in an electric tumble dryer. The resulting dry fabrics have low perfume odor, but when the fabrics are wetted, a noticeably stronger perfume odor is obtained.

COMPLEX 3

Orange Flavor/$\beta$-Cyclodextrin Complex

A complex of food grade, cold-press, orange oil and betacyclodextrin is prepared by a process like that described hereinbefore for Complex 1.

EXAMPLE 41

One part of Complex 3 is mixed with about 3 parts of molten polyethylene glycol with average MW of about 1,450 at about 70° C.

EXAMPLE 42

The molten composition of Example 41 is printed on paper by a hot metal roller to deposit about 0.5 mg of said composition per 1 cm² of paper. The resulting paper has low orange aroma and/or flavor when dry, but gives a noticeable orange flavor and aroma when the paper is moistened with the tongue.

What is claimed is:

1. Composition which exists in liquid form at a temperature between about room temperature and about 100° C. consisting essentially of active-ingredient/cyclodextrin inclusion complex suspended in polyalkylene glycol carrier material, any polar solvent in said composition being at a level that is less than that of said carrier, and the ratio of said complex to said carrier, including any polar solvent that is present, being from about 1:1 to about 1:5.

2. The composition of claim 1 wherein said cyclodextrin is selected from the group consisting of: unsubstituted cyclodextrins containing from about six to about twelve glucose units; derivatives of said unsubstituted cyclodextrins; oligomers, cooligomers, polymers and copolymers of said cyclodextrins; and mixtures thereof, and wherein said cyclodextrin is capable of forming inclusion complexes with said active ingredient.

3. The composition of claim 2 wherein at least a major portion of said cyclodextrin is selected from the group consisting of alpha-cyclodextrin; beta-cyclodextrin; gamma-cyclodextrin; and mixtures thereof.

4. The composition of claim 3 wherein at least a major portion of said cyclodextrin is beta-cyclodextrin.

5. The composition of claim 4 wherein said active-ingredient is perfume.

6. The composition of claim 5 wherein at least a major portion of said perfume is selected from the group consisting of: highly volatile perfume; moderately volatile perfume; and mixtures thereof.

7. The composition of claim 1 wherein said polyalkylene glycol is selected from the group consisting of:

(A) polyalkylene glycols having an average molecular weight of from about 400 to about 20,000 wherein said alkylene glycols are selected from the group consisting of ethylene glycol, propylene glycol, tetramethylene glycol, and mixtures thereof;

(B) $C_1$-$C_{22}$ alkyl ethers and diethers of the polyalkylene glycols having average molecular weights of from about 90 to about 20,000, the average molecular weight being above about 120 when the polyalkylene glycol is polyethylene glycol;

(C) polyalkyoxylated materials having an average molecular weight of from about 200 to about 20,000 wherein the polyalkoxy portion is from about 50% to about 99% of said materials and each alkoxy group contains from two to four carbon atoms; and (D) mixtures thereof.

8. The composition of claim 7 wherein said polyalkylene glycol is (A).

9. The composition of claim 7 wherein said polyalkylene glycol is (B).

10. The composition of claim 7 wherein said polyalkylene glycol is (C).

11. The composition of claim 1 wherein said polyalkylene glycol is liquid at some temperature which is less than about 100° C.

12. The composition of claim 11 wherein said polyalkylene glycol is liquid at some temperature which is less than about 80° C.

13. The composition of claim 1 wherein said carrier is polyethylene glycol having an average molecular weight of from about 600 to about 20,000.

14. The composition of claim 13 wherein said polyethylene glycol has an average molecular weight of from about 1,000 to about 9,000.

15. A solid fabric conditioning composition comprising from about 30% to about 99% of fabric softening agent and at least an effective amount of the composition of claim 1, wherein said active-ingredient is perfume.

16. The composition of claim 15 wherein at least a major portion of said perfume is selected from the group consisting of: highly volatile perfume; moderately volatile perfume; and mixtures thereof, and said polyalkylene glycol is polyethylene glycol.

17. The composition of claim 16 wherein at least a major portion of said perfume is highly volatile perfume.

18. The composition of claim 15 wherein said polyalkylene glycol is selected from the group consisting of:

(A) polyalkylene glycols having an average molecular weight of from about 400 to about 20,000 wherein said alkylene glycols are selected from the group consisting of ethylene glycol, propylene glycol, tetramethylene glycol, and mixtures thereof;

(B) $C_1$-$C_{22}$ alkyl ethers and diethers of the polyalkylene glycols having an average molecular weights of from about 90 to about 20,000, the average molecular weight being above about 120 when the polyalkylene glycol is polyethylene glycol;

(C) polyalkyoxylated materials having an average molecular weight of from about 200 to about 20,000 wherein the polyalkoxy portion is from about 50% to about 99% of said materials and each alkoxy group contains from two to four carbon atoms; and (D) mixtures thereof.

19. The composition of claim 18 wherein said fabric conditioning composition additionally comprises an effective amount of nonionic softening agent.

20. The composition of claim 1 wherein said active-ingredient is selected from the group consisting of perfumes, flavors, pharmaceuticals, biocontrol agents, and mixtures thereof.

21. The composition of claim 20 wherein said cyclodextrin is selected from the group consisting of: unsubstituted cyclodextrins containing from about six to about twelve glucose units; derivatives of said unsubstituted cyclodextrins; oligomers, cooligomers, polymers and copolymers of said cyclodextrins; and mixtures thereof, and wherein said cyclodextrin is capable of forming inclusion complexes with said active-ingredient.

22. The composition of claim 21 wherein at least a major portion of said cyclodextrin is selected from the group consisting of alpha-cyclodextrin; beta-cyclodextrin; gamma-cyclodextrin; and mixtures thereof.

23. The composition of claim 22 wherein at least a major portion of said cyclodextrin is beta-cyclodextrin.

24. The composition of claim 20 wherein said polyalkylene glycol is liquid below about 100° C.

25. The composition of claim 20 wherein said polyalkylene glycol is solid at normal temperatures.

26. The composition of claim 20 wherein said active-ingredient/cyclodextrin complex is particulate.

27. The composition of claim 26 wherein at least a major portion of said active-ingredient/cyclodextrin complex has a particle size less than about 15 microns.

28. The composition of claim 26 wherein said complex has a particle size of from about 15 microns to about 250 microns.

29. The composition of claim 26 wherein said active-ingredient/cyclodextrin complex has particles ranging in size between about 0.01 micron to about 1,000 microns with substantial amounts both below and above about 15 microns.

30. An article of manufacture comprising:

I. a fabric conditioning composition comprising:
 i. from about 30% to about 99% of fabric softening agent; and
 ii. an effective amount of perfume/cyclodextrin complex in at least about twice its weight of polyalkylene glycol carrier; and II. a dispensing means which provides for release of an effective amount of said composition to fabrics in the dryer at automatic dryer operating temperatures, e.g., 35° C. to 115° C.

* * * * *